US011639497B2

(12) United States Patent
Boer et al.

(10) Patent No.: US 11,639,497 B2
(45) Date of Patent: May 2, 2023

(54) UDP-GLYCOSYLTRANSFERASES

(71) Applicant: DSM IP ASSETS B.V., Heerlen (NL)

(72) Inventors: Viktor Marius Boer, Echt (NL); Johannes Gustaaf Ernst Van Leeuwen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 398 days.

(21) Appl. No.: 16/624,072

(22) PCT Filed: Jun. 26, 2018

(86) PCT No.: PCT/EP2018/067061
§ 371 (c)(1),
(2) Date: Dec. 18, 2019

(87) PCT Pub. No.: WO2019/002264
PCT Pub. Date: Jan. 3, 2019

(65) Prior Publication Data
US 2021/0147816 A1    May 20, 2021

(30) Foreign Application Priority Data

Jun. 27, 2017 (EP) .................... 17178168

(51) Int. Cl.
| | | |
|---|---|---|
| C12N 15/00 | (2006.01) | |
| C12N 9/10 | (2006.01) | |
| A23K 20/163 | (2016.01) | |
| A23L 29/30 | (2016.01) | |
| A23L 27/30 | (2016.01) | |
| A23L 2/60 | (2006.01) | |
| C12N 9/02 | (2006.01) | |
| C12P 19/56 | (2006.01) | |

(52) U.S. Cl.
CPC .......... *C12N 9/1051* (2013.01); *A23K 20/163* (2016.05); *A23L 2/60* (2013.01); *A23L 27/36* (2016.08); *A23L 29/30* (2016.08); *C12N 9/0042* (2013.01); *C12P 19/56* (2013.01); *C12Y 204/01* (2013.01); *A23V 2002/00* (2013.01)

(58) Field of Classification Search
CPC .. C12P 19/56; C12P 15/00; A23L 2/60; C12N 9/1051; C12N 15/70; C12N 9/1029; C12Y 402/03019; C12Y 114/13078; C12Y 204/00; C12Y 114/11023
USPC ..... 435/320.1; 536/23.2, 127, 252.3, 254.11, 536/200
See application file for complete search history.

(56) References Cited

U.S. PATENT DOCUMENTS

| | | | |
|---|---|---|---|
| 10,273,519 B2 | 4/2019 | Broers et al. | |
| 10,472,661 B2 | 11/2019 | Van Den Berg et al. | |
| 2015/0031868 A1 | 1/2015 | Lehmann et al. | |
| 2019/0226000 A1 | 7/2019 | Broers et al. | |

FOREIGN PATENT DOCUMENTS

| | | |
|---|---|---|
| CN | 110100006 A | 8/2019 |
| WO | 2013110673 A1 | 8/2013 |
| WO | 2015/011209 A1 | 1/2015 |
| WO | 2016/055578 A1 | 4/2016 |
| WO | 2018083338 A1 | 5/2018 |

OTHER PUBLICATIONS

Witkowski et al., Biochemistry 38:11643-11650, 1999.*
Kisselev L., Structure, 2002, vol. 10: 8-9.*
Whisstock et al., Quarterly Reviews of Biophysics 2003, vol. 36 (3): 307-340.*
Devos et al., Proteins: Structure, Function and Genetics, 2000, vol. 41: 98-107.*
Cardunculus Cynara: "UNIPARC: UPI00076BF874", Apr. 13, 2016, XP055400202, Retrieved from the Internet: URL: http://www.uniprot.org/uniparc/UPI00076BF874.
Tang, et al., "UDP-glucosyitransferase family protein [Medicago truncatula]", Aug. 25, 2015, XP055400243, Retrieved from the Internet: URL:https://www.ncbi.nlm.nih.gov/protein/XP_013451917.
Theobroma Cacao (cacao): "PREDICTED: UDP-glycosyltransferase 74F2 [Theobroma cacao] XP_007033645", Sep. 12, 2016, XP055400246, Retrieved from the Internet: URL:https://www.ncbi.nlm.nih.gov/protein/XP_007033645.
Altschul, Stephen F. et al., "Basic Local Alignment Search Tool", Journal of Molecular Biology, 1990, pp. 403-410, vol. 215.
Altschul, Stephen F. et al., "Gapped BLAST and PSI-BLAST: a new generation of protein database search programs", Nucleic Acid Research, 1997, pp. 3389-3402, vol. 25, No. 17.
Fierro, Francisco et al., "Autonomously replicating plasmids carrying the AMA1 region in Penicillium chrysogenum", Current Genetics, 1996, pp. 482-489, vol. 29.
Fleer, R. et al., "Stable Multicopy Vectors for High-Level Secretion of Recombinant Human Serum Albumin by Kluyveromyces Yeasts", Bio/Technology, Oct. 1991, pp. 968-975.

(Continued)

*Primary Examiner* — Robert B Mondesi
*Assistant Examiner* — Mohammad Y Meah
(74) *Attorney, Agent, or Firm* — McBee Moore & Vanik IP, LLC

(57) ABSTRACT

The present disclosure relates a polypeptide having UGT activity, which polypeptide comprises an amino acid sequence which, when aligned with a polypeptide having UGT activity comprising the sequence set out in SEQ ID NO: 2, comprises at least one substitution of an amino acid corresponding to any of amino acids at positions
35, 189, 280, 284, 285, 334 or 373,
said positions being defined with reference to SEQ ID NO: 2 and wherein the polypeptide has one or more modified properties as compared with a reference polypeptide having UGT activity. A polypeptide according to the disclosure may be used in a recombinant cell for the production of steviol or a steviol glycoside.

10 Claims, 1 Drawing Sheet

Specification includes a Sequence Listing.

(56) References Cited

OTHER PUBLICATIONS

Humphrey, Tania V. et al., "Spatial organisation of four enzymes from Stevia rebaudiana that are involved in stevioi glycoside synthesis", Plant Molecular Biology, 2006, pp. 47-62, vol. 61.

Kruskal, Joseph B., "Chapter One: An Overview of Sequence Comparison", pp. 1-44.

Mohamed, Amal A.A. et al., "UDP-dependent glycosyltransferases involved in the biosynthesis of stevioi glycosides", Journal of Plant Physiology, 2011, pp. 1136-1141, vol. 168.

Needleman, Saul B. et al., "A General Method Applicable to the Search for Similarities in the Amino Acid Sequence of Two Proteins", Journal of Molecular Biology.

Rice, Peter et al., "EMBOSS: The European Molecular Biology Open Software Suite", The European Molecular Biology Open Software Suite, Jun. 2000, pp. 276-277, vol. 16, No. 6.

Richman, Alex et al., "Functional genomics uncovers three glucosyltransferases involved in the synthesis of the major sweet glucosides of Stevia rebaudiana", The Plant Journal, 2005, pp. 56-67, vol. 41.

Shirley, Renee L. et al., "Nuclear Import of Upf3p Is Mediated by Importin-$\alpha/\beta$ and Export to the Cytoplasm is Required for a Functional Nonsense-Mediated mRNA Decay Pathway in Yeast", Genetics, Aug. 2002, pp. 1465-1482, vol. 161.

Verduyn, Cornelis et al., "Effect of Benzoic Acid on Metabolic Fluxes in Yeasts: A Continuous-Culsture Study on the Regulation of Respiration and Alcoholic Fermentation", Yeast, 1992, pp. 501-517, vol. 8.

Brandle et al., "Steviol glycoside biosynthesis," Phytochemistry, 2007, 68: 1855-1863.

Li et al., "Study of steviol glycoside biosynthesis pathway and the advances in its bioconversion strategies," Food and Fermentation Industries, College of Biological and Environmental Engineering, Zhejiang University of Technology—Hangzhou, 2015, 41(9): 236-242, with English abstract.

* cited by examiner

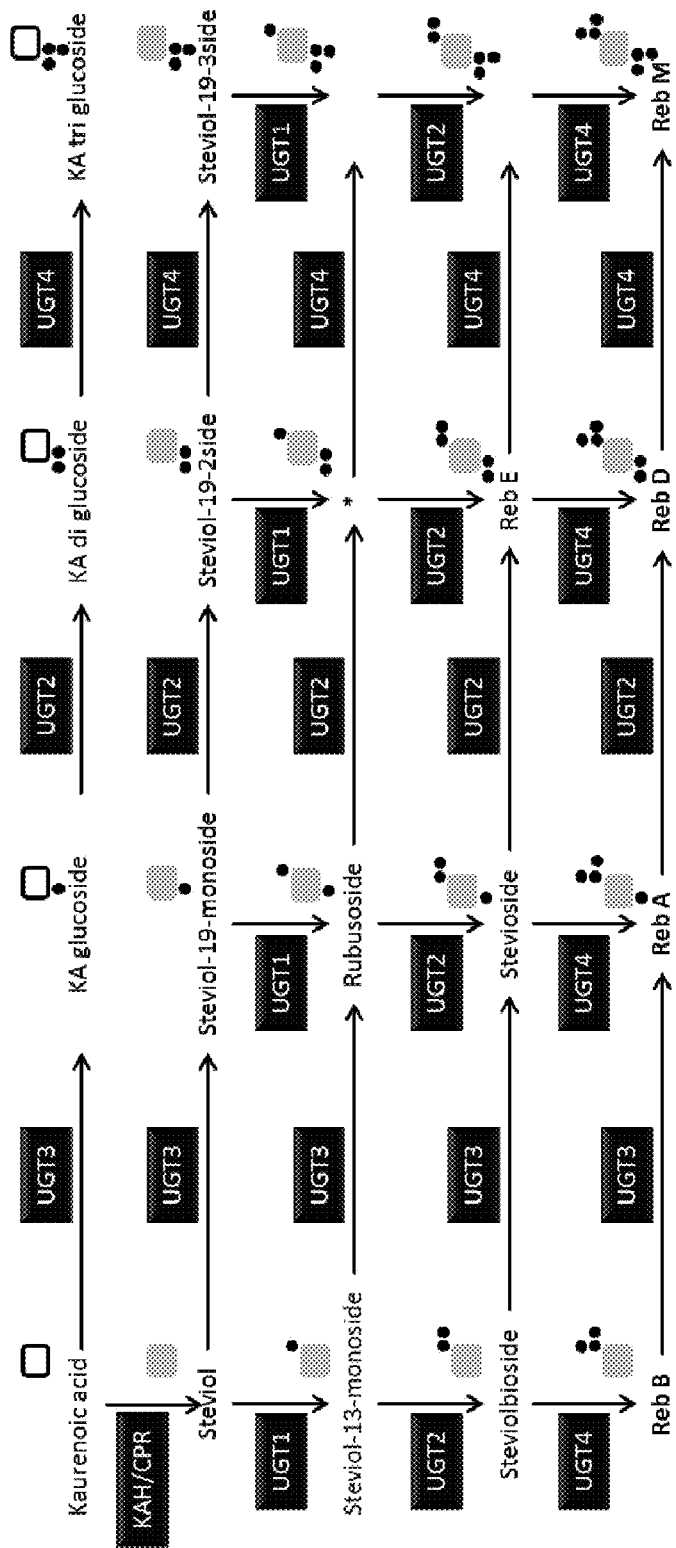

UDP-GLYCOSYLTRANSFERASES

CROSS-REFERENCE TO RELATED APPLICATIONS

This application is a National Stage entry of International Application No. PCT/EP2018/067061, filed 26 Jun. 2018, which claims priority to European Patent Application No. 17178168.5, filed 27 Jun. 2017. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-517000_ST25.txt" created on 5 Dec. 2019 and 87,748 bytes in size) is submitted concurrently with the instant application, and the entire contents of the Sequence Listing are incorporated herein by reference.

BACKGROUND

Field

The present disclosure relates to a polypeptide having UGT activity and to a nucleic acid sequence encoding such a polypeptide. The disclosure also relates to a recombinant cell comprising the nucleic acid sequence, optionally which is capable of producing steviol or a steviol glycoside. The disclosure further relates to a process for the preparation of a steviol glycoside which process comprises culturing the recombinant cell, to a broth comprising a steviol glycoside obtainable by such a process and to a composition comprising one or more steviol glycosides obtained by the process or obtained from the broth. In addition, the disclosure relates to a foodstuff, feed or beverage which comprises such a composition. Further, the disclosure relates to a method for converting steviol or a first steviol glycoside into a steviol glycoside or a second steviol glycoside respectively

Description of Related Art

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A, rebaudioside D and rebaudioside M.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides and/or steviol glycosides produced with lower amounts of undesirable by-products.

DESCRIPTION OF THE FIGURES

FIG. 1 set out a schematic diagram of some, but not all, of the potential pathways leading to biosynthesis of steviol glycosides.

DESCRIPTION OF THE SEQUENCE LISTING

SEQ ID NO: 1 sets out the nucleotide sequence encoding a UGT3 polypeptide from *Stevia rebaudiana*, codon-pair optimized for expression in *Yarrowia lipolytica*.

SEQ ID NO: 2 sets out the amino acid sequence of a UGT3 polypeptide from *Stevia rebaudiana*.

SEQ ID NOs: 3 to 20 are described in Table 2.

SEQ ID NO: 21 sets out the nucleotide sequence encoding a hydroxymethylglutaryl-CoA reductase polypeptide from *Yarrowia lipolytica*, codon-pair optimized for expression in *Yarrowia lipolytica*.

SEQ ID NO: 22 sets out the nucleotide sequence encoding a geranylgeranyl diphosphate synthase polypeptide from *Yarrowia lipolytica*, codon-pair optimized for expression in *Yarrowia lipolytica*.

SEQ ID NO: 23 sets out the nucleotide sequence encoding a copalyl pyrophosphate synthase polypeptide from *Stevia rebaudiana*, codon-pair optimized for expression in *Yarrowia lipolytica*.

SEQ ID NO: 24 sets out the nucleotide sequence encoding a kaurene synthase polypeptide from *Stevia rebaudiana*, codon-pair optimized for expression in *Yarrowia lipolytica*.

SEQ ID NO: 25 sets out the nucleotide sequence encoding a kaurene oxidase polypeptide from *Giberella fujikuroi*, codon-pair optimized for expression in *Yarrowia lipolytica*.

SEQ ID NO: 26 sets out the nucleotide encoding the KAH4 polypeptide codon-pair optimized for expression in *Yarrowia lipolytica*.

SEQ ID NO: 27 sets out the nucleotide sequence encoding a cytochrome P450 reductase polypeptide from *Arabidopsis thaliana*, codon-pair optimized for expression in *Yarrowia lipolytica*.

SEQ ID NO: 28 sets out the nucleotide sequence encoding a UDP-glucosyltransferase polypeptide from *Stevia rebaudiana*, codon-pair optimized for expression in *Yarrowia lipolytica*.

SEQ ID NO: 29 sets out the nucleotide sequence encoding a variant of UDP-glucosyltransferase polypeptide from *Stevia rebaudiana*, codon-pair optimized for expression in *Yarrowia lipolytica*.

SEQ ID NO: 30 sets out the nucleotide sequence encoding a UDP-glucosyltransferase polypeptide from *Stevia rebaudiana*, codon-pair optimized for expression in *Yarrowia lipolytica*.

SEQ ID NO: 31 sets out the sequence of the pHSP promoter.

SEQ ID NO: 32 sets out the sequence of the pgmT terminator.

SEQ ID NO: 33 sets out the nucleotide sequence of the pAgos_lox TEF1 promoter.

SEQ ID NO: 34 sets out the nucleotide sequence of the Agos tef1 Ts_lox terminator.

SUMMARY

The present disclosure is based on the identification of new UDP-glycosyltransferase (UGT) polypeptides, i.e. new polypeptides having UDP-glycosyltransferase (UGT) activity. These polypeptides may be used in the production of recombinant cells suitable for the production of steviol and/or one or more steviol glycosides.

Such recombinant cells may produce higher amounts of steviol glycosides and lower amount of non-desirable products as compared with recombinant cells expressing a reference UGT. Production of higher amounts of steviol glycosides and/or lower amount of non-desirable products may make recovery of steviol glycosides easier. Also, a higher yield may be obtained.

Accordingly, the disclosure relates to a polypeptide having UGT activity, which polypeptide comprises an amino acid sequence which, when aligned with a UGT comprising the sequence set out in SEQ ID NO: 2 (a wild type UGT3/UGT74G1 sequence from *S. rebaudiana*), comprises at least one substitution of an amino acid corresponding to any of amino acids at positions:
35, 189, 280, 284, 285, 334 or 373
said positions being defined with reference to SEQ ID NO: 2 and wherein the polypeptide has one or more modified properties as compared with a reference polypeptide having UGT activity.

The disclosure also relates to:
a polypeptide having UGT activity comprising an amino acid sequence having at least about 95% sequence identity, at least 96%, at least 97%, at least 98% or at least 99% sequence identity to any one of SEQ ID NOs: 4, 6, 8, 10, 12, 14, 16, 18 or 20;
a nucleic acid sequence encoding a polypeptide having UGT activity according to the disclosure;
a recombinant cell comprising a nucleic acid sequence according to the disclosure, optionally which is capable of producing steviol or a steviol glycoside;
a process for the preparation of a steviol glycoside which process comprises culturing a recombinant cell according to the disclosure in a suitable medium under conditions conducive to production of a steviol glycoside, and, optionally, recovering the steviol glycoside;
a broth comprising a steviol glycoside obtainable by the process for the preparation of a steviol glycoside according to the disclosure
a composition comprising one or more steviol glycosides obtained by a process for the preparation of a steviol glycoside according to the disclosure or obtained from a broth comprising a steviol glycoside according to the disclosure;
a foodstuff, feed or beverage which comprises a composition comprising one or more steviol glycosides according to the disclosure; and
a method for converting steviol or a first steviol glycoside into a steviol glycoside or a second steviol glycoside respectively, which method comprises:
contacting steviol or a first steviol glycoside with a recombinant cell according to the disclosure or a permeabilized form thereof, a crude extract or cell free extract derived from such a recombinant cell or an enzyme preparation derived from any thereof;
thereby to convert the steviol or first steviol glycoside into the steviol glycoside or the second steviol glycoside respectively.

BRIEF DESCRIPTION OF THE DRAWINGS

FIG. 1 set out a schematic diagram of some, but not all, of the potential pathways leading to biosynthesis of steviol glycosides.

DETAILED DESCRIPTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

"Rebaudioside" herein may be abbreviated to "Reb" or "reb" or the like.

According to the disclosure, there is thus provided a polypeptide having UDP-glycosyltransferase (UGT) activity, such as UGT3/UGT74G1 activity. A polypeptide having UGT3/UGT74G1 activity is for example the UDP-glycosyltransferase 74G1 from *Stevia rebaudiana* (as described in Richman et al. "The Plant Journal" (2005) 41: 56-67). A polypeptide according to the disclosure has UGT activity, such as UGT3/UGT74G1 activity. UGT activity is the activity of mediating the transfer of glycosyl residues from an activated nucleotide sugar, i.e. from a uridine-diphosphate-activated monosaccharide, e.g. uridine-diphosphate-5'-glucose (UDPG), to an acceptor molecule (aglycones). Herein, the aglycone may preferably be steviol or a steviol glycoside. The sugar residue donor may preferably be UDP-glucose. However, UGT activity for the purposes of this disclosure also cover activity where in the sugar residue donor is, for example, UDP-galactose, UDP-xylose, UDP-rhamnose or UDP-glucoronate.

UGT3 or UGT74G1 activity may be the activity of catalyzing the addition of a C-19-glucose to steviolbioside, i.e. it may be the activity of catalysing the addition of a glucose unit to the 19-COOH of the steviol backbone in steviolbioside. That is to say, a UGT3/UGT74G1 may be capable of catalyzing a reaction in which steviolbioside is converted to stevioside.

UGT3 or UGT74G1 activity may also be the activity of transferring a glucose unit to the 13-OH or the 19-COOH, respectively, of steviol. That is to say, a UGT3/UGT74G1 may be capable of catalyzing a reaction in which steviol is converted to steviolmonoside, preferably wherein steviol is converted to steviol-19-monoside.

UGT3 or UGT74G1 activity may be the activity of catalyzing the addition of a C-19-glucose to steviol. That is to say, a UGT3/UGT74G1 may be capable of catalyzing a reaction in which steviol is converted to steviol-19-monoside.

UGT3 or UGT74G1 activity may be the activity of catalyzing the addition of a C-19-glucose to rebaudioside B. That is to say, a UGT3/UGT74G1 may be capable of catalyzing a reaction in which rebaudioside B is converted into rebaudioside A.

A UGT3/UGT74G1 may function as a uridine 5'-diphospho glucosyl:steviol 19-COOH transferase and a uridine 5'-diphospho glucosyl:steviol-13-O-glucoside 19-COOH transferase.

Functional UGT3//UGT74G1 polypeptides also may catalyze glycosyl transferase reactions that utilize steviol glycoside substrates other than steviol, steviol-13-O-glucoside and steviolbioside, or that transfer sugar moieties from donors other than uridine diphosphate glucose.

Thus, for the purposes of the disclosure, a polypeptide having UGT activity may be one which is capable of catalysing or partially catalyzing the formation of a steviol glycoside from steviol or a second steviol glycoside from a first steviol glycoside. For the purposes of the disclosure therefore, a polypeptide may be one having UGT activity, i.e. one which is capable of catalysing or partially catalyzing the formation of a steviol glycoside from steviol or a steviol glycoside.

A polypeptide according to the disclosure has modified UGT activity as compared with a reference polypeptide having UGT activity.

Such a polypeptide may have a decreased specific UGT activity as compared with the reference polypeptide.

Such a polypeptide may have an increased specific UGT activity as compared with the reference polypeptide.

A polypeptide according to the disclosure may be a non-naturally occurring polypeptide.

Herein, polypeptides according to the disclosure may be referred to as a "UGT", "UGT enzyme" or "UGT polypeptide". Herein, "UGT3", "UGT3 enzyme" or "UGT3 polypeptide" mean the same as UGT74G1", "UGT74G1 enzyme" or "UGT74 polypeptide".

A UGT polypeptide according to the disclosure (for example a polypeptide having one or more substitution as set out herein) may comprise an amino acid sequence having at least about 60%, 70%, 80% identity with the reference UGT polypeptide, such as the UGT of SEQ ID NO: 2, for example at least about 85% identity with the parent polypeptide, such as at least about 90% identity with the parent polypeptide, at least about 95% identity with the parent polypeptide, at least about 98% identity with the parent polypeptide or at least about 99% identity with the parent polypeptide. Such a UGT polypeptide will typically have one or more substitution or sets of substitutions selected from a position corresponding to 35, 189, 280, 284, 285, 334 or 373 as defined with reference to SEQ ID NO: 2.

An amino acid position corresponding to one of the positions defined herein in the reference UGT may be a position that aligns in a multiple (protein) sequence alignment with any of the stated amino acid positions.

An amino acid position corresponding to one of the positions 35, 189, 280, 284, 285, 334 or 373, said position being defined with reference to SEQ ID NO: 2, is a position which is identified in the UGT polypeptide sequence when the latter is aligned with the amino acid sequence set out in SEQ ID NO: 2 by a suitable sequence alignment method. A suitable sequence alignment method is a method which allows comparison of the sequences with each other and identifications of the positions in the amino acid sequence of the UGT polypeptide wherein either the same amino acid is present (identical position), or another amino acid is present (substitution), or one or more extra amino acids are present (insertion or extension) or no amino acid is present (deletion or truncation) if compared with the amino acid sequence set out in SEQ ID NO: 2.

A suitable method allowing comparison of two amino acid sequence may be any suitable Pairwise Sequence Alignment method known to those skilled in the art, preferably a Global Pairwise Sequence Alignment method. A preferred Global Pairwise Sequence Alignment method is the EMBOSS Needle method based on the Needleman-Wunsch alignment algorithm (aiming at finding the optimum alignment (including gaps) of the two sequences along their entire length) (Needleman, S. B. and Wunsch, C. D. (1970) J. Mol. Biol. 48, 443-453) as described herein. In one embodiment, the amino acid sequence is aligned with the amino acid sequence set out in SEQ ID NO: 2 using the EMBOSS Needle alignment method using EBLOSUM62 as a substitution matrix, preferably with a gap-open penalty of 10 and a gap extension penalty of 0.5.

In one embodiment according to the disclosure, the positions in the polypeptide having UGT activity corresponding to any amino acids at position 35, 189, 280, 284, 285, 334 or 373, said position being defined with reference to SEQ ID NO: 2, are identified by aligning the amino acid sequence of the polypeptide with UGT activity of the disclosure with the amino acid sequence set out in SEQ ID NO: 2 using the EMBOSS Needle alignment method, such as the NEEDLE program from the EMBOSS package, using EBLOSUM62 as a substitution matrix, with a gap-open penalty of 10 and a gap extension penalty of 0.5.

A UGT according to the disclosure will typically retain UGT activity. That is to say, a UGT according to the disclosure will typically be capable of catalysing the reactions set out above, albeit with a modified activity as compared with a reference polypeptide.

Preferably, a UGT polypeptide according to the disclosure will typically exhibit improved properties in comparison with the reference polypeptide from which it is derived, typically in terms of specific activity and/or substrate specificity. Such an improved property will typically be one which is relevant if the UGT were to be used as set out below, for example in a method for the production of steviol and/or a steviol glycoside (by expressing the UGT in a recombinant cell).

Thus, a UGT according to the disclosure is one which is typically capable of increasing production of steviol and/or a steviol glycoside in a recombinant cell capable of the production of said steviol and/or a steviol glycoside (in comparison with a recombinant cell capable of the production of steviol and/or a steviol glycoside which expresses the reference polypeptide). That is to say, overexpression of a UGT polypeptide according to the disclosure in a recombinant cell will typically lead to increased production of steviol and/or a steviol glycoside as compared to a cell which overexpresses the reference polypeptide (such as the UGT3 of SEQ ID NO: 2).

A UGT according to the disclosure may be one which is typically capable of decreasing production of a non-steviol glycoside, such as one or more kaurenoic acid glycosides, in a recombinant cell capable of the production of steviol and/or a steviol glycoside (in comparison with a recombinant cell capable of the production of steviol and/or a steviol glycoside which expresses the reference polypeptide). That is to say, overexpression of a UGT polypeptide according to the disclosure in a recombinant cell will typically lead to increased production of steviol and/or a steviol glycoside as compared to a recombinant cell which overexpresses the reference polypeptide (such as the UGT3 of SEQ ID NO: 2).

Production of lower amounts of non-steviol glycoside products may make recovery of steviol glycosides easier. Also, a higher yield may be obtained.

A UGT which exhibits a property which is improved in relation to the reference UGT is one which demonstrates a measurable reduction or increase in the relevant property, for example specific activity, typically such that the UGT is more suited to a use as set out herein, for example in a method for the production of steviol or a steviol glycoside.

A UGT polypeptide according to the disclosure comprises an amino acid sequence that has one or more substitution, deletion and/or insertion of an amino acid as compared to the reference polypeptide and/or one or more truncations as compared to the reference polypeptide. A UGT polypeptide may comprise one or more of the substitutions described herein.

A polypeptide having UGT activity, for example as set out herein, which polypeptide comprises an amino acid sequence which, when aligned with the UGT comprising the sequence set out in SEQ ID NO: 2, comprises at least one substitution of an amino acid corresponding to any of amino acids 35, 189, 280, 284, 285, 334 or 373
said positions being defined with reference to SEQ ID NO: 2 and wherein the UGT has one or more modified properties as compared with a reference polypeptide having UGT activity.

In one embodiment, the reference polypeptide having UGT activity is the polypeptide with amino acid sequence according to SEQ ID NO: 2.

Substitution of an amino acid is intended to indicate that the amino acid residue at the specified position is replaced with a different amino acid.

Accordingly, a polypeptide having UGT activity, for example as set out herein, which polypeptide comprises an amino acid sequence which, when aligned with the UGT comprising the sequence set out in SEQ ID NO: 2, comprises at least one substitution of an amino acid residue corresponding to any of amino acids 35, 189, 280, 284, 285, 334 or 373
said positions being defined with reference to SEQ ID NO: 2 and wherein the UGT has one or more modified properties as compared with a reference polypeptide having UGT activity.

Thus, the amino acid present at one or more of the said positions will be replaced with a different amino acid than appears at that position in the reference sequence (the positions being defined with reference to SEQ ID NO: 2).

A UGT polypeptide according to the disclosure may comprise one of the substitutions set out above, or may comprise any combination of two, three, four, five, six or all of them.

A UGT polypeptide according to the disclosure may be one wherein:
(i) a valine is present at position 35;
(ii) an alanine is present at position 189;
(iii) an asparagine is present at position 280;
(iv) an asparagine is present at position 284;
(v) a glycine is present at position 285
(vi) an asparagine is present at position 285
(vii) a serine is present at position 285
(viii) an alanine is present at position 334; and/or
(ix) an alanine is present at position 373.
said positions being defined with reference to SEQ ID NO: 2.

Any combination of the above defined substitutions may be used to define a UGT polypeptide according to the disclosure.

Thus, a UGT polypeptide according to the disclosure may comprise an amino acid sequence which, when aligned with the UGT comprising the sequence set out in SEQ ID NO: 2, comprises at least the following substitutions of an amino acid corresponding to any of amino acids:

35 and 189; 35 and 280; 35 and 284; 35 and 285; 35 and 334; 35 and 373; 189 and 280; 189 and 284; 189 and 285; 189 and 334; 189 and 373; 280 and 284; 280 and 285; 280 and 334; 280 and 373; 284 and 285; 284 and 334; 284 and 373; 285 and 334; 285 and 373; 334 and 373; 35, 189 and 280; 35, 189 and 284; 35, 189 and 285; 35, 189 and 334; 35, 189 and 373; 35, 280 and 284, 35, 280 and 285, 35, 280 and 334; 35, 280 and 373; 35, 284 and 285; 35, 284 and 334; 35, 284 and 373; 35, 285 and 334; 35, 285 and 373; 35, 334 and 373; 189, 280 and 284; 189, 280 and 285; 189, 280 and 334; 189, 280 and 373; 189, 284 and 285; 189, 284 and 334; 189, 284 and 373; 189, 285 and 334; 189, 285 and 373; 189, 334 and 373; 280, 284 and 285; 280, 284 and 334; 280, 284 and 373; 280, 285 and 334; 280, 285 and 373; 280, 334 and 373; 284, 285 and 334; 284, 285 and 373; 284, 334 and 373; or 285, 334 and 373.

said positions being defined with reference to SEQ ID NO: 2.

A UGT polypeptide according to the disclosure may comprise additional substitutions other than one or more of the seven substitutions positions defined above, for example, one or more additional substitutions, additions or deletions.

A UGT according to the disclosure may comprise a combination of different types of modification of this sort. A UGT may comprise one, two, three, four, at least 5, at least 10, at least 15, at least 20, at least 25, at least 30 or more such modifications (which may all be of the same type or may be different types of modification). Typically, the additional modifications may be substitutions.

A UGT polypeptide according to the disclosure may comprise the amino acid sequence set out in any one of SEQ ID NOs: 4, 6, 8, 10, 12, 14, 16, 18 or 20. However, a UGT polypeptide may comprise any combination of substitutions at positions 35, 189, 280, 284, 285, 334 or 373, said positions being defined with reference to a suitable reference sequence such as that set out in SEQ ID NO: 2.

A recombinant cell according to the disclosure may comprise nucleic acid sequences encoding one, two, three, four, five or more UGTs according to the disclosure. Such UGT polypeptides may be the same or different. A recombinant cell may comprise a nucleic acid sequence encoding a UGT3 comprising the amino acid sequence of SEQ ID NO: 2 and a nucleic acid sequence encoding one or more UGTs according to the disclosure. That is to say, a cell may comprise a nucleic acid sequence encoding the UGT comprising the amino acid sequence of SEQ ID NO: 2 and nucleic acid sequences encoding one or more UGTs according to the disclosure, each of which may be present in a copy of one, two, three, four, five or more.

A UGT polypeptide will typically have modified UGT activity in comparison to a reference polypeptide. Typically, the modified activity may be defined in terms of steviol and/or steviol glycoside production in a recombinant cell.

The modified activity may be defined in terms of an increase in the production of steviol and/or a steviol glycoside when a UGT is overexpressed in a recombinant cell as compared to the production level of an equivalent cell which overexpresses a reference polypeptide, for example that of SEQ ID NO: 2.

The modified activity may be defined in terms of a decrease in the production of a non-steviol glycoside, such as a non-desirable product such as a kaurenoic acid glycoside, when a UGT is overexpressed in a recombinant cell as compared to the production level of an equivalent cell which overexpresses a reference polypeptide, for example that of SEQ ID NO: 2.

The modified activity may be defined in terms of a change in ratio of the production of two steviol glycosides, for example the ratio of rebaudioside A:rebaudioside M may be increased or, alternatively, the ratio of rebaudioside M:rebaudioside A may be increased, when a UGT is overexpressed in a recombinant cell as compared to the production level of an equivalent cell which overexpresses a reference polypeptide, for example that of SEQ ID NO: 2.

The modified activity may be defined in terms of a change in ratio of the sum of steviol glycosides produced to the sum of kaurenoic acid-glycosides, for example the ratio of the sum of steviol glycosides:the sum of kaurenoic acid-glycosides may be increased when a UGT is overexpressed in a recombinant cell as compared to the production level of an equivalent cell which overexpresses a reference polypeptide, for example that of SEQ ID NO: 2.

The modified activity may also be defined in terms of increased stability of a UGT, for example having a longer half-life than a reference polypeptide, for example that of SEQ ID NO: 2.

A UGT may be capable of increasing production levels, for example by at least 5%, at least 10%, at least 25%, at least 50%, at least 100% or more. Production levels may be expressed in terms of g/L or mol/L (M), so an increase in the production level of steviol and/or steviol glycosides will be evident by higher level of production in terms of g/L or mol/L.

In the case of a non-desirable product, such as one or more kaurenoic acid glycosides, a UGT may be capable of decreasing production levels for example by at least 5%, at least 10%, at least 25%, at least 50% or more. A UGT may be capable of decreasing this ratio, for example by at least 1%, at least 2%, at least 5%, at least 10%, at least 25%, at least 50%, at least 100% or more.

As set out above, this may also be defined in terms of an increase in the sum of steviol glycosides:the sum of kaurenoic acid-glycosides.

The word "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd ed. Cold Spring Harbor Laboratory, Cold Spring Harbor Laboratory Press, Cold Spring Harbor, N.Y., 1989).

A UGT polypeptide according to the disclosure may be in isolated form, such as substantially isolated form. By "isolated" polypeptide or protein is intended a polypeptide or protein removed from its native environment. For example, recombinantly produced polypeptides and proteins expressed in cells are considered isolated for the purpose of the disclosure as are recombinant polypeptides which have been substantially purified by any suitable technique. A UGT polypeptide according to the disclosure can be recovered and purified from recombinant cell cultures by methods known in the art.

UGT polypeptides of the present disclosure include products of chemical synthetic procedures, and products produced by recombinant techniques from a prokaryotic or eukaryotic cell, including, for example, bacterial, yeast, higher plant, insect and mammalian cells. Depending upon the cell employed in a recombinant production procedure, the polypeptides of the present disclosure may be glycosylated or may be non-glycosylated. In addition, polypeptides according to the disclosure may also include an initial modified methionine residue, in some cases as a result of cell-mediated processes.

The disclosure also features biologically active fragments of the UGT polypeptides according to the disclosure. Such fragments are considered to be encompassed within the term "a UGT according to the disclosure".

Biologically active fragments of a UGT polypeptide according to the disclosure include polypeptides comprising amino acid sequences sufficiently identical to or derived from the amino acid sequence of a UGT protein according to the disclosure which include fewer amino acids than the full-length protein but which exhibit at least one biological activity of the corresponding full-length protein. Typically, biologically active fragments comprise a domain or motif with at least one activity of a UGT protein according to the disclosure. A biologically active fragment of a UGT according to the disclosure can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide according to the disclosure.

Typically, a protein fragment of a UGT according to the disclosure will comprise one or more of the substitutions defined herein.

The disclosure also features a nucleic acid sequence encoding the above biologically active fragments (which biologically active fragments are themselves UGTs according to the disclosure).

The present disclosure provides nucleic acid sequences encoding a UGT polypeptide according to the disclosure (and biologically active fragments thereof). The disclosure also relates to an isolated nucleic acid sequence encoding at least one functional domain of a UGT polypeptide UGT according to the disclosure. Typically, such a domain will comprise one or more of the substitutions described herein. Such a nucleic acid sequence according to the disclosure may be non-naturally occurring.

A nucleic acid sequence of the present disclosure can be generated using standard molecular biology techniques well known to those skilled in the art taken in combination with the sequence information provided herein. For example, using standard synthetic techniques, the required nucleic acid molecule may be generated by PCR or synthesized de novo. Such a synthetic process will typically be an automated process.

A nucleic acid sequence according to the disclosure may comprise one or more deletions, i.e. gaps, in comparison to a nucleic acid sequence encoding a reference UGT. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleic acid sequences according to the disclosure can be prepared by standard synthetic techniques, e.g., using an automated DNA synthesizer.

Also, complementary nucleic acids and antisense nucleic acids are included in the present disclosure. A nucleic acid molecule which is complementary to a nucleic acid sequence is one which is sufficiently complementary to the nucleic acid sequence such that it can hybridize to at least a part of the nucleic acid sequence forming a stable duplex.

One aspect of the disclosure pertains to isolated polynucleotides or nucleic acids that encode a UGT polypeptide according to the disclosure, or a biologically active fragment or domain thereof, as well as nucleic acid molecules sufficient for use as hybridization probes to identify nucleic acid molecules encoding a polypeptide according to the disclosure and fragments of such nucleic acid molecules suitable for use as PCR primers for the amplification or mutation of nucleic acid molecules, such as for the preparation of nucleic acid molecules according to the disclosure.

As used herein, the terms "polynucleotide", "nucleic acid" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated polynucleotide" or "isolated nucleic acid" typically is a DNA or RNA that is not immediately contiguous with both of the non-coding sequences with which it is immediately contiguous (one on the 5' end and one on the 3' end) in the naturally occurring genome of the organism from which it is derived. Thus, in one embodiment, an isolated polynucleotide or nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated polynucleotide fragment" or "isolated nucleic acid fragment" is typically a fragment that is not naturally occurring as a fragment and would not be found in the natural state.

The disclosure also relates to a nucleic acid construct comprising a polynucleotide comprising a nucleotide sequence encoding a UGT polypeptide according to the disclosure and, linked operably thereto, control sequences permitting expression of the nucleic acid sequence in a cell. The nucleic acid construct may be incorporated into a vector, such as an expression vector and/or into a cell in order to effect expression of the UGT polypeptide.

The term "nucleic acid construct" is herein referred to as a nucleic acid molecule, either single- or double-stranded, which is isolated from a naturally-occurring gene or, more typically, which has been modified to contain segments of nucleic acid sequence(s) which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

As used herein, the term "operably linked" refers to a linkage of nucleic acid sequence elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleic acid sequence coding for an enzyme such as a UGT polypeptide or any other enzyme introduced in a recombinant cell according to the disclosure, may be not native to a nucleic acid sequence coding for the enzyme to be expressed, i.e. a promoter that is heterologous to the nucleic acid sequence (coding sequence) to which it is operably linked.

Suitable promoters in this context include both constitutive and inducible natural promoters as well as engineered promoters, which are well known to the person skilled in the art. Suitable promoters in cells may be GAL7, GAL10, or GAL1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleic acid sequence encoding an enzyme comprises a terminator. Any terminator, which is functional in a cell, may be used in the present disclosure. Preferred terminators are obtained from natural genes of the cell. Suitable terminator sequences are well known in the art. Preferably, such terminators are combined with mutations that prevent nonsense mediated mRNA decay in the recombinant cell according to the disclosure (see for example: Shirley et al., 2002, Genetics 161:1465-1482).

The disclosure further relates to a vector, preferably an expression vector, comprising a nucleic acid sequence or a nucleic acid construct according to the disclosure (i.e. comprising sequence encoding a UGT polypeptide according to the disclosure).

In order to facilitate expression and/or translation of the UGT, the nucleic acid sequence encoding the UGT may be comprised in an expression vector such that the gene encoding the UGT is operably linked to the appropriate control sequences for expression and/or translation in vitro, or in a recombinant cell according to the disclosure. That is to say, the disclosure provides an expression vector comprising a nucleic acid sequence or nucleic acid construct according to the disclosure.

The expression vector may be any vector (e.g., a plasmid or virus), which can be conveniently subjected to recombinant DNA procedures and can bring about the expression of the nucleic acid sequence encoding the UGT polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a cell of fungal origin, a suitable episomal nucleic acid construct may e.g. be based on the yeast 2µ or pKD1 plasmids (Gleer et al., 1991, Biotechnology 9: 968-975), or the AMA plasmids (Fierro et al., 1995, Curr Genet. 29:482-489).

Alternatively, the expression vector may be one which, when introduced into a cell, is integrated into the genome and replicated together with the chromosome(s) into which it has been integrated. The integrative cloning vector may integrate at random or at a predetermined target locus in the chromosomes of the cell. In a preferred embodiment according to the disclosure, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the cell, i.e. integration in a predetermined target locus, is increased by augmented homologous recombination abilities of the host cell.

The homologous flanking DNA sequences in the cloning vector, which are homologous to the target locus, may be derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l. More typically, the target locus may be an intergenic location, so that a gene is not interrupted. Such a locus may also provide for high expression levels. Accordingly, the homologous flanking DNA sequences in the cloning vector may be homologous to an intergenic target locus A nucleic acid construct or expression vector may be assembled in vivo in a host cell according to the disclosure and, optionally, integrated into the genome of the cell in a single step (see, for example, WO2013/076280)

More than one copy of a nucleic acid construct or expression vector according to the disclosure may be inserted into a host cell to increase production of the UGT polypeptide (overexpression) encoded by the nucleic acid sequence comprised within the nucleic acid construct. This can be done, preferably by integrating into its genome two or more copies of the nucleic acid, more preferably by targeting the integration of the nucleic acid to a locus defined as defined above.

It will be appreciated by those skilled in the art that the design of the expression vector can depend on such factors as the choice of the host cell to be transformed, the level of expression of protein desired, etc. The expression vectors according to the disclosure can be introduced into host cells to thereby produce proteins or peptides, encoded by nucleic acids as described herein (e.g. a UGT of SEQ ID NO: 2, for example a functional equivalent or fragment, or a fusion protein comprising one or more of such UGTs).

The nucleic acid constructs and vectors according to the disclosure can be designed for expression of UGT polypeptides according to the disclosure in a prokaryotic host cell or eukaryotic host cell.

A nucleic acid construct and/or expression vector according to the disclosure can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a cell well known to those skilled in the art. Suitable methods for transforming or transfecting cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

"Functional equivalents" according to the disclosure are isolated nucleic acid fragments that encode a polypeptide that exhibits a particular function of a UGT according to the disclosure as defined herein. Functional equivalents therefore also encompass biologically active fragments and are themselves encompassed within the term "a UGT" (or the like) according to the disclosure.

Preferably, a functional equivalent according to the disclosure comprises one or more of the substitutions described herein. However, a functional equivalent may comprise one or more modifications in addition to the substitutions described above.

Functional nucleic acid equivalents may typically contain silent mutations or mutations that do not alter the biological function of the encoded UGT polypeptide. Accordingly, the disclosure provides nucleic acid molecules encoding a UGT protein that contains changes in amino acid residues that are not essential for a particular biological activity, i.e. UGT activity.

Such functional equivalents of UGT proteins differ in amino acid sequence from the parent UGT sequence from which they are derived yet retain at least one biological activity thereof, preferably they retain at least UGT activity. The skilled person will recognise that changes can be introduced by mutation into the nucleic acid sequences according to the disclosure thereby leading to changes in the amino acid sequence of the resulting protein without substantially altering the function of such a protein.

In one embodiment the isolated nucleic acid molecule comprises a nucleic acid sequence encoding a protein, wherein the protein comprises an amino acid sequence having at least about 60%, 65%, 70%, 75%, 80%, 85%, 90%, 95%, 96%, 97%, 98%, 99% identity with the parent UGT or to the reference amino acid sequence (for example that shown in SEQ ID NO: 2.

Accordingly, a functional equivalent of a UGT according to the disclosure is preferably a protein which comprises an amino acid sequence having at least about 60%, 65%, 70%, 75%, 80%, 85%, 90%, 95%, 96%, 97%, 98%, 99% or more identity to the parent UGT amino acid sequence or reference polypeptide sequence, for example that shown in SEQ ID NO: 2, and typically also retains at least one functional activity of the parent UGT polypeptide.

A polypeptide according to the disclosure having UGT activity may comprise an amino acid sequence having at least about 80% sequence identity, at least about 90% sequence identity, at least about 95% sequence identity, at least about 96%, at least about 97%, at least about 98% or at least about 99% sequence identity to any one of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 or SEQ ID NO: 20.

A UGT polypeptide according to the disclosure may have a sequence as defined in Table 2 or a substitution pattern as defined in Table 2 (in terms of position(s), if not precisely the same amino acid substitution).

UGT polypeptides according to the disclosure may be identified e.g. by screening libraries of mutants, e.g. substitution mutants, of a suitable reference polypeptide. Candidate mutants may be screened on the basis of their ability to increase steviol or steviol glycoside production, when expressed in a recombinant cell (in comparison with a corresponding cell expressing the reference polypeptide).

Fragments of a nucleic acid according to the disclosure may comprise or consist of sequences not encoding functional polypeptides. Such nucleic acids may function as probes or primers for a PCR reaction.

Nucleic acids according to the disclosure irrespective of whether they encode functional or non-functional polypeptides can be used as hybridization probes or polymerase chain reaction (PCR) primers. Uses of the nucleic acid molecules of the present disclosure that do not encode a polypeptide having UGT activity include, inter alia, (1) in situ hybridization (e.g. FISH) to metaphase chromosomal spreads to provide precise chromosomal location of an UGT-encoding gene as described in Verma et al., Human Chromosomes: a Manual of Basic Techniques, Pergamon Press, New York (1988); (2) Northern blot analysis for detecting expression of UGT mRNA in specific tissues and/or cells; and (3) probes and primers that can be used as a diagnostic tool to analyse the presence of a nucleic acid hybridizable to such a probe or primer in a given biological (e.g. tissue) sample.

A UGT according to the disclosure based on a given reference UGT enzyme can be obtained by the following standard procedure:
  Mutagenesis (error-prone, doped oligo, spiked oligo) or synthesis of variants
  Transformation in, for example, Y. lipolytica or S. cerevisiae
  Cultivation of transformants, selection of transformants
  Expression in, for example, Y. lipolytica or S. cerevisiae
  Primary Screening, for example on the basis of steviol or steviol glycoside production
  Identification of an improved UGT In one embodiment the disclosure relates to a method of producing a UGT polypeptide according to the disclosure, which method comprises:

a) selecting a reference UGT polypeptide (i.e. a template or starting polypeptide);
b) substituting at least one amino acid residue corresponding to any of
   35, 189, 280, 284, 285, 334 or 373
   said positions being defined with reference to SEQ ID NO: 2;
c) optionally substituting one or more further amino acids as defined in b);
d) preparing the UGT resulting from steps a)-c);
e) determining a property of the UGT, for example as set out in the Examples; and
f) selecting a UGT with an altered property in comparison to the reference UGT polypeptide.

In a preferred embodiment in the method of producing a UGT polypeptide according to the disclosure, the reference UGT polypeptide has the sequence set out in SEQ ID NO: 2

More preferably in step b) of the method according to the disclosure at least one amino acid residue corresponding to any of
   35, 189, 280, 284, 285, 334 or 373
   is substituted, said positions being defined with reference to SEQ ID NO: 2 The reference polypeptide may have at least about 80% homology with SEQ ID NO: 2.

In another embodiment, the disclosure features cells, e.g., transformed cells or recombinant cells that contain a nucleic acid, nucleic acid construct or vector according to the disclosure. A "recombinant cell" or "host cell" according to the disclosure is typically a cell into which (or into an ancestor of which) has been introduced, by means of recombinant DNA techniques, a nucleic acid according to the disclosure, i.e. a nucleic acid encoding a UGT according to the disclosure. In the context of the present disclosure a "cell" according to the disclosure or a parent of said cell may be any type of cell.

Thus, a cell according to the disclosure may comprise a recombinant nucleic acid encoding one or more UGT polypeptides according to the disclosure.

A cell according to the disclosure may be a eukaryotic or a prokaryotic cell. Accordingly, both prokaryotic and eukaryotic cells are included, e.g., bacteria, fungi, yeast, and the like, especially preferred are cells from yeasts, for example, S. cerevisiae, Y. lipolytica and K. lactis. Host cells also include, but are not limited to, mammalian cell lines such as CHO, VERO, BHK, HeLa, COS, MDCK, 293, 3T3, W138, and choroid plexus cell lines.

The disclosure thus provides a method for producing a UGT, which method comprises cultivating a recombinant cell as described herein under conditions suitable for production of the UGT and, optionally, recovering the UGT. Typically the recombinant cell is capable of producing steviol or a steviol glycoside.

A recombinant cell according to the disclosure may comprise any polypeptide as described herein. Typically, a recombinant cell according to the disclosure is capable of producing a steviol glycoside. Typically, a recombinant cell according to the disclosure is capable of producing a glycosylated diterpene, such as a steviol glycoside. For example, a recombinant cell according to the disclosure may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebaudioside A, rebaudioside E, rebaudioside D or rebaudioside M.

A recombinant cell according to the disclosure may comprise one or more recombinant nucleic acid sequences encoding one or more polypeptides having UDP-glycosyltransferase (UGT) activity.

For the purposes of this disclosure, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 1 sets out a schematic diagram of steviol glycoside formation.

A recombinant cell according to the disclosure may thus comprise one or more recombinant nucleic acid sequences encoding one or more of:
(i) a polypeptide having UGT2 activity;
(ii) a polypeptide having UGT85C2 activity; and
(iii) a polypeptide having UGT76G1 activity.

A recombinant cell according to the disclosure may comprise a recombinant nucleic acid sequence encoding a polypeptide having UGT74G1 activity, other than a UGT polypeptide according to the disclosure. That is to say, a recombinant cell according to the disclosure may comprise a nucleic acid sequence or sequences comprising two or more different polypeptides having UGT activity, one being a UGT polypeptide according to the disclosure.

A recombinant yeast suitable for use in the disclosure may comprise a nucleic acid sequence encoding a polypeptide capable of catalyzing the addition of a C-13-glucose to steviol. That is to say, a recombinant yeast suitable for use in a method according to the disclosure may comprise a UGT which is capable of catalyzing a reaction in which steviol is converted to steviolmonoside.

Such a recombinant yeast suitable for use in a method according to the disclosure may comprise a nucleic acid sequence encoding a polypeptide having the activity shown by UDP-glycosyltransferase (UGT) UGT85C2, whereby the nucleic acid sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5-diphospho glucosyl:steviol 13-OH transferase, and a uridine 5'-diphospho glucosyl:steviol-19-O-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the disclosure may comprise a nucleic acid sequence encoding a polypeptide which has UGT2 activity.

A polypeptide having UGT2 activity is one which functions as a uridine 5'-diphospho glucosyl:steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl:rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D.

A polypeptide having UGT2 activity may also transfer sugar moieties from donors other than uridine diphosphate glucose. For example, a polypeptide having UGT2 activity act as a uridine 5'-diphospho D-xylosyl:steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl:steviol-13-O-glucoside transferase, transferring a rhamnose moiety to the C-2' of the 13-O-glucose of the acceptor molecule, steviol.

A recombinant yeast suitable for use in a method the disclosure may comprise a nucleic acid sequence encoding a polypeptide capable of catalyzing glucosylation of the C-3' of the glucose at the C-13 position of stevioside. That is to say, a recombinant yeast suitable for use in a method according to the disclosure may comprise a UGT which is capable of catalyzing a reaction in which stevioside is converted to rebaudioside A. Accordingly, such a recombinant yeast may be capable of converting stevioside to rebaudioside A. Expression of such a nucleic acid sequence may confer on the yeast the ability to produce at least rebaudioside A.

A recombinant yeast suitable for use in a method the disclosure may comprise a nucleic acid sequence encoding a polypeptide capable of catalyzing glycosylation of the C-3' of the glucose at the C-19 position of rebaudioside D. That is to say, a recombinant yeast suitable for use in a method according to the disclosure may comprise a UGT which is capable of catalyzing a reaction in which rebaudioside D is converted to rebaudioside M. Accordingly, such a recombinant yeast may be capable of converting rebaudioside D to rebaudioside M. Expression of such a nucleic acid sequence may confer on the yeast the ability to produce at least rebaudioside M.

A recombinant yeast suitable for use in a method according to the disclosure may thus also comprise a nucleic acid sequence encoding a polypeptide having the activity shown by UDP-glycosyltransferase (UGT) UGT76G1, whereby the nucleic acid sequence upon transformation of a yeast confers on that yeast the ability to convert stevioside to rebaudioside A or rebaudioside D to rebaudioside M.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl:steviol 13-O-1,2 glucoside C-3 ' glucosyl transferase and a uridine 5'-diphospho glucosyl:steviol-19-O-glucose, 13-O-1,2 bioside C-3' glucosyl transferase. Functional UGT76G1 polypeptides may also catalyze glycosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method according to the disclosure typically comprises nucleic acid sequences encoding at least one polypeptide having UGT1 activity, at least one polypeptide having UGT2 activity, at least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid may encode a polypeptide which has two, three or four of the activities set out above. Preferably, a recombinant yeast for use in the method according to the disclosure comprises UGT1, UGT2 and UGT3 and UGT4 activity. Suitable UGT1, UGT2, UGT3 and UGT4 sequences are described in Table 1 of WO2015/007748.

A recombinant cell according to the disclosure may comprise two or more nucleic acid sequences encoding a polypeptide having any one UGT activity, for example UGT1, 2, 3 or 4, activity. Where a recombinant cell according to the disclosure comprises two or more nucleic acid sequences encoding a polypeptide having any one UGT activity, those nucleic acid sequences may be the same or different and/or may encode the same or different polypeptides. For example, a recombinant cell according to the disclosure may comprise a nucleic acid sequence encoding two different UGT2 polypeptides.

A recombinant cell according to the disclosure may comprise a recombinant nucleic acid sequence encoding a polypeptide having UGT3 activity, other than a UGT3 according to the disclosure. That is to say, a recombinant cell according to the disclosure may comprise a nucleic acid sequence or sequences comprising two or more different polypeptides having UGT activity one being a UGT polypeptide according to the disclosure.

A recombinant cell according to the disclosure may comprise one or more recombinant nucleic acid sequence(s) encoding one of more of:
 a polypeptide having ent-copalyl pyrophosphate synthase activity;
 a polypeptide having ent-Kaurene synthase activity;
 a polypeptide having ent-Kaurene oxidase activity; and
 a polypeptide having kaurenoic acid 13-hydroxylase activity.

For the purposes of this disclosure, a polypeptide having ent-copalyl pyrophosphate synthase (EC 5.5.1.13) is capable of catalyzing the chemical reaction:

This enzyme has one substrate, geranylgeranyl pyrophosphate, and one product, ent-copalyl pyrophosphate. This enzyme participates in gibberellin biosynthesis. This enzyme belongs to the family of isomerases, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this disclosure, a polypeptide having ent-kaurene synthase activity (EC 4.2.3.19) is a polypeptide that is capable of catalyzing the chemical reaction:
 ent-copalyl diphosphate ⇌ ent-kaurene+diphosphate Hence, this enzyme has one substrate, ent-copalyl diphosphate, and two products, i.e. ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleic acid sequence used in a recombinant cell according to the disclosure may encode a polypeptide having ent-copalyl pyrophosphate synthase activity and ent-kaurene synthase activity. Alternatively, the two activities may be encoded two distinct, separate nucleic acid sequences.

For the purposes of this disclosure, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

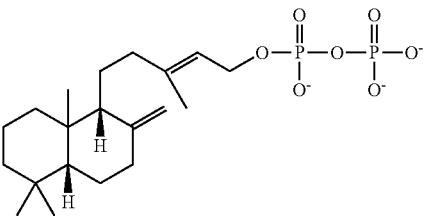

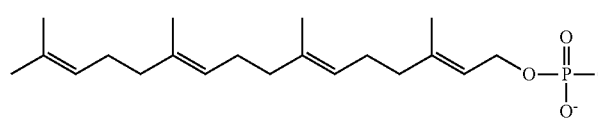

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the disclosure, a polypeptide having kaurenoic acid 13-hydroxylase activity (EC 1.14.13) is one which is capable of catalyzing the formation of steviol (ent-kaur-16-en-13-o1-19-oic acid) using NADPH and O2. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant cell according to the disclosure may comprise a recombinant nucleic acid sequence encoding a polypeptide having NADPH-cytochrome p450 reductase activity. That is to say, a recombinant cell according to the disclosure may be capable of expressing a nucleic acid sequence encoding a polypeptide having NADPH-cytochrome p450 reductase activity. For the purposes of the disclosure, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the host cell from a FAD- and FMN-containing enzyme NADPH:cytochrome P450 reductase (POR; EC 1.6.2.4).

In a recombinant cell according to the disclosure, the ability of the cell to produce geranylgeranyl diphosphate (GGPP) may be upregulated. Upregulated in the context of this disclosure implies that the recombinant cell produces more GGPP than an equivalent non-recombinant cell.

Accordingly, a recombinant cell according to the disclosure may comprise one or more nucleic acid sequence(s) encoding hydroxymethylglutaryl-CoA reductase, farnesyl-pyrophosphate synthetase and geranylgeranyl diphosphate synthase, whereby the nucleic acid sequence(s) upon transformation of the microorganism confer(s) on the microorganism the ability to produce elevated levels of GGPP. Thus, a recombinant cell according to the disclosure may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant cell according to the disclosure may comprise nucleic acid sequences encoding one or more of:
  a polypeptide having hydroxymethylglutaryl-CoA reductase activity;
  a polypeptide having farnesyl-pyrophosphate synthetase activity;
  a polypeptide having geranylgeranyl diphosphate synthase activity.

A host cell herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant cell is one which is genetically modified or transformed/transfected with one or more of the nucleic acid sequences as defined herein. The term recombinant cell herein also encompasses cells which have been modified using genome editing techniques such as CRISPR-Cas The presence of the one or more such nucleic acid sequences as defined herein may alter the ability of the microorganism to produce steviol or a steviol glycoside, in particular one or more steviol glycosides. A non-recombinant cell, i.e. one that is not transformed/transfected or genetically modified, typically does not comprise one or more of the nucleic acid sequences enabling the cell to produce a steviol glycoside. Hence, a non-recombinant cell is typically a cell that does not naturally produce a steviol glycoside, although a cell which naturally produces a steviol or a steviol glycoside and which has been modified according to the disclosure (and which thus has an altered ability to produce a steviol glycoside) is considered a recombinant cell according to the disclosure.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and NADPH-cytochrome p450 reductase are native to the cell and that transformation with one or more of the nucleic acid sequences encoding these enzymes may not be required to confer on the cell the ability to produce steviol or a steviol glycoside. A preferred cell according to the present disclosure may be a recombinant cell which is naturally capable of producing GGPP (i.e. in its non-recombinant form).

Further improvement of steviol or steviol glycoside production by the host microorganism may be obtained by classical strain improvement.

A host cell may be a prokaryotic, archaebacterial or eukaryotic host cell.

A prokaryotic host cell may be, but is not limited to, a bacterial host cell. A eukaryotic host cell may be, but is not limited to, a yeast, a fungus, an amoeba, an algae, an animal, an insect host cell.

A eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus* nigerCBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

A eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus,*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., Choroflexus bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

The disclosure further provides a method for producing a polypeptide according to the disclosure comprising:
(a) cultivating a recombinant cell according to the disclosure under conditions conducive to the production of the polypeptide by the recombinant cell, and optionally,
(b) recovering the polypeptide.

A recombinant cell according to the present disclosure may be able to grow on any suitable carbon source known in the art and convert it to a steviol glycoside. The recombinant cell may be able to convert directly plant biomass, celluloses, hemicelluloses, pectines, rhamnose, galactose, fucose, maltose, maltodextrines, ribose, ribulose, or starch, starch derivatives, sucrose, glucose, lactose or glycerol. Hence, a preferred cell expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the cell is able to convert a carbon source selected from the group consisting of glucose, xylose, arabinose, sucrose, lactose and glycerol. The cell may for instance be a eukaryotic cell as described in WO03/062430, WO06/009434, EP1499708B1, WO2006096130 or WO04/099381.

Thus, in a further aspect, the disclosure also provides a process for the preparation of a steviol glycoside which process comprises culturing a recombinant cell according to the disclosure in a suitable medium under conditions conducive to production of a steviol glycoside, and, optionally, recovering the steviol glycoside.

The term steviol glycoside may be Rebaudioside A (RebA) (CAS #58543-16-1), Rebaudioside B (RebB) (CAS #58543-17-2), Rebaudioside C (RebC) (CAS #63550-99-2), Rebaudioside D (RebD) (CAS #63279-13-0), Rebaudioside E (RebE) (CAS #63279-14-1), Rebaudioside F (RebF) (CAS #438045-89-7), Rebaudioside M (RebM) (CAS #1220616-44-3), Rubusoside (CAS #63849-39-4), Dulcoside A (CAS #64432-06-0), Rebaudioside I (RebI) (MassBank Record: FU000332), Rebaudioside Q (RebQ), 1,2-Stevioside (CAS #57817-89-7), 1,3-Stevioside (RebG), 1,2-bioside (MassBank Record: FU000299), 1,3-bioside, Steviol-13-O-glucoside (13-SMG), Steviol-19-O-glucoside (19-SMG), a tri-glucosylated steviol glycoside, a tetra-glycosylated steviol glycoside, a penta-glucosylated steviol glycoside, a hexa-glucosylated steviol glycoside, a hepta-glucosylated steviol glycoside, and isomers thereof.

The medium used in the process for the production of a steviol glycoside may be any suitable medium which allows growth of a particular recombinant cell according to the disclosure. The essential elements of the medium are known to the person skilled in the art and may be adapted to the recombinant cell selected.

Preferably, the medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, glucose, sucrose, lactose, fatty acids, triglycerides and glycerol. Preferably, the medium also comprises a nitrogen source such as urea, or an ammonium salt such as ammonium sulphate, ammonium chloride, ammonium nitrate or ammonium phosphate.

The process according to the present disclosure may be carried out in batch, fed-batch or continuous mode. A separate hydrolysis and fermentation (SHF) process or a simultaneous saccharification and fermentation (SSF) process may also be applied. A combination of these process modes may also be possible for optimal productivity. A SSF process may be particularly attractive if starch, cellulose, hemicelluose or pectin is used as a carbon source in the process, where it may be necessary to add hydrolytic enzymes, such as cellulases, hemicellulases or pectinases to hydrolyse the substrate.

The recombinant cell used in the process for the preparation of a steviol glycoside may be any suitable recombinant cell as defined herein above. It may be advantageous to use a recombinant eukaryotic cell according to the disclosure in the process since most eukaryotic cells do not require sterile conditions for propagation and are insensitive to bacteriophage infections. In addition, eukaryotic cells may be grown at low pH to prevent bacterial contamination.

The recombinant cell according to the present disclosure may be a facultative anaerobic microorganism. A facultative anaerobic recombinant cell can be propagated aerobically to a high cell concentration. This anaerobic phase can then be carried out at high cell density which reduces the volume required substantially, and may minimize the risk of contamination with aerobic microorganisms.

The process for the production of a steviol glycoside according to the present disclosure may be an aerobic or an anaerobic process.

An anaerobic process may be herein defined as a process run in the absence of oxygen or in which substantially no oxygen is consumed, preferably less than 5, 2.5 or 1 mmol/Uh, and wherein organic molecules serve as both electron donor and electron acceptors. The process according to the present disclosure may also first be run under aerobic conditions and subsequently under anaerobic conditions.

The process may also be run under oxygen-limited, or micro-aerobical, conditions. Alternatively, the process may first be run under aerobic conditions and subsequently under oxygen-limited conditions. An oxygen-limited process is a process in which the oxygen consumption is limited by the oxygen transfer from the gas to the liquid. The degree of oxygen limitation is determined by the amount and composition of the ingoing gasflow as well as the actual mixing/mass transfer properties of the equipment used.

The production of a steviol glycoside in the process according to the present disclosure may occur during the growth phase of the cell, during the stationary (steady state) phase or during both phases. It may be possible to run the process at different temperatures.

The process for the production of a steviol glycoside may be run at a temperature which is optimal for the recombinant cell. The optimum growth temperature may differ for each transformed recombinant cell and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant cell.

The process for the production of a steviol glycoside according to the present disclosure may be carried out at any suitable pH value. If the recombinant cell is a yeast, the pH in the medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the process at these low pH values is that growth of contaminant bacteria in the medium may be prevented.

Such a process may be carried out on an industrial scale. The product of such a process is one or more steviol glycosides, such one or more of, for example, steviol-13-monoside, steviol-19-monoside, 13-[(β-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebaudiosideA, rebaudiosideE, rebaudiosideD or rebaudiosideM.

Recovery of steviol glycoside(s) from the medium may be performed by known methods in the art, for instance by distillation, vacuum extraction, solvent extraction, or evaporation.

In the process for the production of a steviol glycoside according to the disclosure, it may be possible to achieve a concentration of above 5 mg/l broth, preferably above 10 mg/l, preferably above 20 mg/l, preferably above 30 mg/l broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, but usually below 70 g/l.

The disclosure further provides a broth comprising a steviol glycoside obtainable by the process according to the disclosure for the preparation of a steviol glycoside.

A broth according to the disclosure may comprises a recombinant cell according to the disclosure. Alternatively, a broth according to the disclosure may be one from which all recombinant cells according to the disclosure are absent or substantially absent, for example a supernatant.

In the event that one or more steviol glycosides is expressed within the microorganism, such cells may need to be treated so as to release them. Preferentially, at least one steviol glycoside, for example rebA, reb D or rebM, is produced extracellularly.

A broth according to the disclosure may comprise more than at least one steviol glycoside, such as rebA, rebD or rebM, as compared with a broth produced from a recombinant cell in which a reference polypeptide is expressed instead of a polypeptide according to the disclosure.

A broth according to the disclosure may comprise less of at least one non-steviol glycoside, for example one or more kaurenoic acid glycosides, as compared with a broth produced from a recombinant cell in which a reference polypeptide is expressed instead of a polypeptide according to the disclosure.

The disclosure also provides a steviol glycoside obtained by a process according to the disclosure for the preparation of a steviol glycoside or obtainable from a broth according to the disclosure. Such a steviol glycoside may be a non-naturally occurring steviol glycoside, that is to say one which is not produced in plants.

Also provided is a composition, such as a sweetener composition, comprising one or more, for example one or more, steviol glycosides obtainable by a process according to the disclosure for the preparation of a steviol glycoside or obtainable from a broth according to the disclosure. In such a composition, one or more of the steviol glycosides may be a non-naturally occurring steviol glycoside, that is to say one which is not produced in plants.

Furthermore, the disclosure provides a method for converting steviol or a first steviol glycoside into a steviol glycoside or second steviol glycoside respectively, which method comprises:
    contacting said steviol or first steviol glycoside with a recombinant cell according to the disclosure, a cell free extract derived from such a recombinant cell or an enzyme preparation derived from either thereof;
    thereby to convert the first steviol glycoside into the second steviol glycoside.

The first steviol glycoside may be any steviol glycoside, such as one illustrated in FIG. 1.

The second steviol glycoside may be any steviol glycoside producing by action of a UGT enzyme on a first steviol glycoside (for example any steviol glycoside illustrated in FIG. 1).

In such a method, the second steviol glycoside may be, for example, rebA, rebE, rebD or RebM.

In such a method, the first steviol glycoside may be stevioside, rebB, rebA, rebE or rebD and the second steviol glycoside may be rebA, rebD or rebM.

Preferably, the first steviol glycoside is rebA and the second steviol glycoside is rebD or the first steviol glycoside is rebD and the second steviol glycoside is rebM. The first steviol glycoside may be rebB and the second steviol glycoside may be rebA.

That is to say, the disclosure relates to a method of bioconversion or biotransformation.

A steviol glycoside or composition produced by the process according to the present disclosure may be used in any application known for such compounds. In particular, they may for instance be used as a sweetener, for example in a food or a beverage. According to the disclosure therefore, there is provided a foodstuff, feed or beverage which comprises a steviol glycoside or a composition according to the disclosure.

For example a steviol glycoside or a composition according to the disclosure may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic or toothpaste, etc. In addition, a steviol glycoside or a composition according to the disclosure can be used as a sweetener not only for drinks, foodstuffs, and other products dedicated for human consumption, but also in animal feed and fodder with improved characteristics.

Accordingly, the disclosure provides, inter alia, a foodstuff, feed or beverage which comprises a steviol glycoside prepared according to a process according to the disclosure.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A steviol glycoside or a composition according to the disclosure can be used in dry or liquid forms. It can be added before or after heat treatment of food products. The amount of the sweetener depends on the purpose of usage. It can be added alone or in the combination with other compounds.

Compounds produced according to the method according to the disclosure may be blended with one or more further non-caloric or caloric sweeteners. Such blending may be used to improve flavour or temporal profile or stability. A wide range of both non-caloric and caloric sweeteners may be suitable for blending with a steviol glycoside or a composition according to the disclosure. For example, non-caloric sweeteners such as mogroside, monatin, aspartame, acesulfame salts, cyclamate, sucralose, saccharin salts or erythritol. Caloric sweeteners suitable for blending with a steviol glycoside or a composition according to the disclosure include sugar alcohols and carbohydrates such as sucrose, glucose, fructose and HFCS. Sweet tasting amino acids such as glycine, alanine or serine may also be used.

A steviol glycoside or a composition according to the disclosure can be used in the combination with a sweetener suppressor, such as a natural sweetener suppressor. It may be combined with an umami taste enhancer, such as an amino acid or a salt thereof.

A steviol glycoside or a composition according to the disclosure can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a steviol glycoside or a composition according to the disclosure may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A steviol glycoside or a composition according to the disclosure may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a steviol glycoside or a composition according to the disclosure may be used as a sweetener not only for drinks, foodstuffs, and other products dedicated for human consumption, but also in animal feed and fodder with improved characteristics.

The examples of products where a steviol glycoside or a composition according to the disclosure can be used as a sweetening compound can be as alcoholic beverages such as vodka, wine, beer, liquor, sake, etc.; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A steviol glycoside or a composition according to the disclosure can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present disclosure can be made by any method known to those skilled in the art that provide homogenous even or homogeneous mixtures of the ingredients. These methods include dry blending, spray drying, agglomeration, wet granulation, compaction, co-crystallization and the like.

In solid form a steviol glycoside or a composition according to the disclosure can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms "sequence homology" or "sequence identity" are used interchangeably herein. For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice,P. Longden,I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence according to the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labelled in the output of the program as "longest-identity".

The nucleic acid and protein sequences of the present disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules according to the disclosure. BLAST protein searches can be performed with the XBLAST program, score =50, word length=3 to obtain amino acid sequences homologous to protein molecules according to the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

Embodiments According to the Disclosure

1. A polypeptide having UGT activity, which polypeptide comprises an amino acid sequence which, when aligned with a polypeptide having UGT activity comprising the sequence set out in SEQ ID NO: 2, comprises at least one substitution of an amino acid corresponding to any of amino acids at positions 35, 189, 280, 284, 285, 334 or 373 said positions being defined with reference to SEQ ID NO: 2 and wherein the polypeptide has one or more modified properties as compared with a reference polypeptide having UGT activity.

2. A polypeptide according to embodiment 1, wherein the modified property is modified UGT activity.

3. A polypeptide according to embodiment 1 or 2, wherein the UGT activity is UGT3 activity.

4. A polypeptide according to any one of the preceding embodiments, wherein the reference polypeptide comprises the UGT of SEQ ID NO: 2.

5. A polypeptide according to any one of the preceding embodiments, wherein:

(x) a valine is present at position 35;
   (xi) a alanine is present at position 189;
   (xii) an asparagine is present at position 280;
   (xiii) an asparagine is present at position 284;
   (xiv) a glycine is present at position 285
   (xv) an asparagine is present at position 285
   (xvi) a serine is present at position 285
   (xvii) an alanine is present at position 334; and/or
   (xviii) an alanine is present at position 373.
   said positions being defined with reference to SEQ ID NO: 2.

6. A polypeptide according to any one of the preceding embodiments comprising an amino acid sequence having at least 70%, at least 75%, at least 80%, at least 85%, at least 90%, at least 95%, at least 97%, at least 98% or at least 99% sequence identity with SEQ ID NO: 2.

7. A polypeptide having UGT activity comprising an amino acid sequence having at least about 95% sequence identity, at least 96%, at least 97%, at least 98% or at least 99% sequence identity to any one of SEQ ID NOs: 4, 6, 8, 10, 12, 14, 16, 18 or 20.

8. A nucleic acid sequence encoding a polypeptide according to any one of the preceding embodiments.

9. A recombinant cell comprising a nucleic acid sequence according to embodiment 8, optionally which is capable of producing steviol or a steviol glycoside.

10. A recombinant cell according to claim 9 which comprises one or more nucleic acid sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.

11. A recombinant cell according to embodiment 9 or 10, which comprises a nucleic acid sequence encoding a polypeptide having NADPH-cytochrome p450 reductase activity.

12. A recombinant cell according to any one of embodiments 9 to 11 which comprises one or more nucleic acid sequence encoding one or more of:
   (i) a polypeptide having UGT2 activity;
   (ii) a polypeptide having UGT85C2 activity; and
   (iii) a polypeptide having UGT76G1 activity.

13. A recombinant cell according to any one of embodiments 9 to 12, wherein the cell belongs to one of the genera Saccharomyces, Aspergillus, Pichia, Kluyveromyces, Candida, Hansenula, Humicola, Issatchenkia, Trichosporon, Brettanomyces, Pachysolen, Yarrowia, Yamadazyma or Escherichia, for example a Saccharomyces cerevisiae cell, a Yarrowia lipolytica cell, a Candida krusei cell, an Issatchenkia orientalis cell or an Escherichia coli cell.

14. A process for the preparation of a steviol glycoside which process comprises culturing a recombinant cell according to any one of embodiments 9 to 13 in a suitable medium under conditions conducive to production of a steviol glycoside, and, optionally, recovering the steviol glycoside.

15. A broth comprising a steviol glycoside obtainable by the process according to embodiment 14.

16. A composition comprising one or more steviol glycosides obtained by a process according to embodiment 14 or obtained from a broth according to embodiment 15.

17. A foodstuff, feed or beverage which comprises a composition according to embodiment 16.

18. A method for converting steviol or a first steviol glycoside into a steviol glycoside or a second steviol glycoside respectively, which method comprises:
   contacting steviol or a first steviol glycoside with a recombinant cell according to any one of embodiments 9 to 13 or a permeabilized form thereof, a crude extract or cell free extract derived from such a recombinant cell or an enzyme preparation derived from any thereof; thereby to convert the steviol or first steviol glycoside into the steviol glycoside or the second steviol glycoside respectively.

The following Examples illustrate the disclosure:

EXAMPLES

General

Standard genetic techniques, such as overexpression of enzymes in host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1. Deletion of UGT3 from Steviol Glycosides Producing *Yarrowia lipolytica*

For the purpose of testing UGT3 variants, all UGT3 copies were removed from a steviol glycoside producing strain, strain ML15186. Similar strains to ML15186 have been described in more detail in applications in WO2013/110673 and WO2015/007748. Both genomically integrated copies of the UGT3 were removed from strain ML15186 by using standard molecular biological techniques. PCR confirmed their complete deletion. Production experiments of the resulting strain showed the production of steviol 13-monoside, steviolbioside, and RebB. Other steviol glycosides such as steviol-19-monoside, rubusoside, RebA and RebM, as well as glycosylated kaurenoic acid, were absent, illustrating the complete lack of UGT3 activity in this strain. This UGT3-free strain was named STV2181. The gene content of this strain is given below in Table 1.

TABLE 1

Genotype of strain STV2181. Between brackets indicates the gene copy number present in the strain

| Strain name | Genotype |
| --- | --- |
| STV2181 | MATB tHMG (2; SEQ ID NO: 21) GGS (2; SEQ ID NO: 22) CPS (4; SEQ ID NO: 23) KS (4; SEQ ID NO: 24) KO (2; SEQ ID NO: 25) KAH4 (3; SEQ ID NO: 26) CPR3 (2; SEQ ID NO: 27) UGT1 (2; SEQ ID NO: 28) UGT2 (1; SEQ ID NO: 29) UGT4 (2; SEQ ID NO: 30) |

Example 2. UGT3 Variants Expression in Steviol Glycosides Producing *Yarrowia lipolytica*

Expression pathways were constructed with the UGT3 ORF flanked by a pHSP promoter (SEQ ID NO: 31) and pgmT terminator (SEQ ID NO: 32). Next to this expression cassette for UGT3 a dominant resistance marker, KanMX was present, flanked by a promoter (SEQ ID NO: 33) and terminator (SEQ ID NO: 34). The expression pathway further contained homologous flanks at each end for integration at a chosen locus in the genome. The expression pathway was amplified with PCR, and the purified PCR products were transformed to strain STV2181. Transformants were grown on plates containing G418.

The variants that were tested are set out in the following Table 2.

TABLE 2

UGT3 variants

| Variant | Amino Acid Change | SEQ ID NO (amino acid) | SEQ ID NO (nucleotide) |
|---|---|---|---|
| WT | — | 2 | 1 |
| UGT3_1 | I35V | 4 | 3 |
| UGT3_2 | S189A | 6 | 5 |
| UGT3_3 | A280N | 8 | 7 |
| UGT3_4 | L284N | 10 | 9 |
| UGT3_5 | V285G | 12 | 11 |
| UGT3_6 | V285N | 14 | 13 |
| UGT3_7 | V285S | 16 | 15 |
| UGT3_8 | V334A | 18 | 17 |
| UGT3_9 | M373A | 20 | 19 |

Example 3. Production of Steviol Glycosides and Kaurenoic Acid Glycosides in *Yarrowia lipolytica* Expressing UGT3 Variants STV2181 transformed with the different UGT3 variants were plated on YPhD plates containing G418, single colony isolates were obtained, and a production test was performed: as pre-culture 200 µl YEP with glucose was inoculated with colony material from YEPh-D agar plates containing G418. The pre-culture was incubated 72 hours in an Infors incubator at 30° C., 750 rpm and 80% humidity. 40 µl of pre-culture was used to inoculate 2.5 ml mineral medium with glucose as carbon source. These production cultures were incubated 120 hours in an Infors incubator at 30° C., 550 rpm, 80% humidity. The production cultures were pelleted by centrifugation at 3000×g for 10 minutes. After centrifugation supernatant was transferred and diluted in 33% acetonitrile and analyzed for steviol, steviol glycosides, kaurenoic acid (KA) and glycosylated kaurenoic acid (KA-glycosides) using LC/MS. The data in Table 3 represents the average for at least 6 replicates per UGT3 gene variant, and 57 replicates for the UGT3 wild type (SEQ ID NO: 2).

UGT3 variants were selected based on their ability to glycosylate steviol, and their reduced ability to glycosilate kaurenoic acid. This ratio between these two is expressed as Ratio 1:(steviol+steviol-13-monoside+steviol-19-monoside+rubusoside+steviolbioside+stevioside+RebB+RebA+RebE+RebD+RebM)/(kaurenoic acid+kaurenoic acid glucoside+kaurenoic acid di glucoside+kaurenoic acid tri glucoside). The production levels of steviol glycosides, kaurenoic acid glycosides and the ratios were normalized to the strain expressing the wild type UGT3 sequence. Reduced ability to glycosylate kaurenoic acid may coincide with reduced ability to glycosylate steviol, which would be undesired. Hence, these variants should still have sufficient activity to glycosylate the 19 positions of steviol (or alternatively, steviol-13-monoside, steviolbioside and/or RebB). RebA, RebD and RebM are products downstream of UGT3 activity, and these are also included in table 3. The sum RebA, RebD and RebM production is normalized to the production of the strain expressing the wild type UGT3 sequence. What can be seen is that strains expressing the variants included in Table 3 have improved steviol glycoside production and reduced kaurenoic acid glycoside production. As a consequence, they have greatly improved ratios of steviol glycosides over KA glycosides. This increased ratio will be advantageous in the production of steviol glycosides, where the production of kaurenoic acid glycosides are undesired. All the variants listed in Table 3 have improved RebA, RebD and RebM production, indicating an improved activity on steviol (or alternatively, on steviol-13-monoside, steviolbioside and/or RebB). This makes these UGT3 variants very suitable for the production of these steviol glycosides, or steviol glycosides that are produced from RebA, RebD or RebM.

TABLE 3

Normalized production of steviol glycosides and kaurenoic acid glycosides in strain STV2181 transformed with WT UGT3 or UGT3 variants. Total SGs: steviol + steviol-13-monoside + steviol-19-monoside + rubusoside + steviolbioside + stevioside + RebB + RebA + RebE + RebD + RebM. Total KAGs: kaurenoic acid + kaurenoic acid glucoside + kaurenoic acid di glucoside + kaurenoic acid tri glucoside. Ratio 1: Total SGs/Total KAGs, and normalized sum Rebaudioside A, Rebaudioside D and Rebaudioside M production in strain STV2181, transformed with UGT3 genes.

| UGT3 variant | Total SGs (normalized) | Total KAGs (normalized) | Ratio 1 (normalized) | Sum RebA, RebD, RebM (normalized) |
|---|---|---|---|---|
| WT | 1.00 | 1.00 | 1.00 | 1.00 |
| UGT3_1 | 1.05 | 0.97 | 1.08 | 1.13 |
| UGT3_2 | 1.07 | 0.61 | 1.75 | 1.23 |
| UGT3_3 | 1.27 | 0.07 | 18.3 | 1.18 |
| UGT3_4 | 1.31 | 0.14 | 9.41 | 1.29 |
| UGT3_5 | 1.12 | 0.67 | 1.66 | 1.19 |
| UGT3_6 | 1.24 | 0.29 | 4.26 | 1.42 |
| UGT3_7 | 1.20 | 0.32 | 3.79 | 1.26 |
| UGT3_8 | 1.14 | 0.50 | 2.28 | 1.14 |
| UGT3_9 | 1.12 | 0.56 | 2.01 | 1.29 |

Example 4. Production in Bioreactors of Steviol Glycosides and Kaurenoic Acid Glycosides in *Yarrowia lipolytica* Expressing UGT3 Variants Four strains constructed as described above were cultivated in 500 mL shake-flasks with 50 ml mineral medium for 2 days at 30° C. and 280 rpm. Subsequently, 43 ml of the content of the shake-flask was transferred into a fermenter with a starting volume of 0.4 L. The glucose containing mineral medium of the shake flask and fermentation was based on Verduyn et al. (Verduyn C, Postma E, Scheffers W A, Van Dijken J P. Yeast, 1992 Jul. 8(7):501-517). The pH was controlled at 5.7 by addition of ammonia (9 wt %). Temperature was controlled at 30° C. Glucose concentration was kept limited after the batch phase by controlled glucose feed to the fermenter. Broth samples were diluted in water and 33% acetonitrile and analyzed with LC/MS and LC/UV.

The results are set out in Table 4 and show that also in bioreactors the strains expressing the UGT3 variants have greatly reduced production of glycosylated kaurenoic acid, and increased production of steviol glycosides, including the steviol glycosides Rebaudiosde A, D and M. A higher ratio of steviol glycosides over kaurenoic acid glycosides (Ratio 1) is advantageous for steviol glycoside recovery from the fermentation broth and product purification.

TABLE 4

Normalized production of steviol glycosides and kaurenoic acid plycosides in strain STV2181 transformed with WT UGT3 or UGT3 variants in bioreactors. Total SGs: steviol + steviol-13-monoside + steviol-19-monoside + rubusoside + steviolbioside + stevioside + RebB + RebA + RebE + RebD + RebM. Total KAGs: kaurenoic acid + kaurenoic acid glucoside + kaurenoic acid di glucoside + kaurenoic acid tri glucoside. Ratio 1: Total SGs/Total KAGs, and normalized sum Rebaudioside A, Rebaudioside D and Rebaudioside M production in strain STV2181, transformed with UGT3 genes.

| UGT3 variant | Total SGs (normalized) | Total KAGs (normalized) | Ratio 1 (normalized) | Sum RebA, RebD, RebM (normalized) |
|---|---|---|---|---|
| WT | 1.0 | 1.0 | 1.0 | 1.0 |
| UGT3_3 | 1.5 | 0.1 | 18 | 1.3 |
| UGT3_6 | 1.1 | 0.3 | 4.0 | 1.1 |
| UGT3_7 | 1.4 | 0.3 | 4.2 | 1.4 |

The invention claimed is:

1. A nucleic acid sequence encoding a polypeptide having UGT74G1 activity, which polypeptide comprises an amino acid sequence which, when aligned with a polypeptide having UGT activity comprising the sequence of SEQ ID NO:2, comprises at least one substitution of an amino acid corresponding to any of amino acids at positions
35, 189, 280, 284, 285, 334, or 373,
said positions being defined with reference to SEQ ID NO:2 and wherein the polypeptide has:
 an amino acid sequence having at least 90% sequence identity with SEQ ID NO:2; and
 an improved UGT74G1 activity in a recombinant cell capable of steviol glycoside production, in comparison with a recombinant cell capable of such production and which expresses the reference polypeptide of SEQ ID NO:2, said improved UGT74G1 activity in said recombinant cell selected from the group consisting of: increased production of steviol glycoside;
 decreased production of non-steviol glycosides; and increased production of steviol glycoside and decreased production of non-steviol glycosides.

2. A recombinant cell comprising the nucleic acid sequence according to claim 1, optionally which is capable of producing steviol or a steviol glycoside.

3. The recombinant cell according to claim 2, further comprising one or more nucleic acid sequence(s) encoding:
 a polypeptide having ent-copalyl pyrophosphate synthase activity;
 a polypeptide having ent-Kaurene synthase activity;
 a polypeptide having ent-Kaurene oxidase activity; and
 a polypeptide having kaurenoic acid 13-hydroxylase activity.

4. The recombinant cell according to claim 2, further comprising a nucleic acid sequence encoding a polypeptide having NADPH-cytochrome p450 reductase activity.

5. The recombinant cell according to claim 2, further comprising one or more nucleic acid sequence(s) encoding one or more of:

(i) a polypeptide having UGT2 activity;
(ii) a polypeptide having UGT85C2 activity; and
(iii) a polypeptide having UGT76G1 activity.

6. The recombinant cell according to claim 2, wherein the cell belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*, for example a *Saccharomyces cerevisiae* cell, a *Yarrowia* lipolytica cell, a *Candida* krusei cell, an *Issatchenkia orientalis* cell, or an *Escherichia* coli cell.

7. A process for preparation of a steviol glycoside, which process comprises culturing the recombinant cell according to claim 2 in a suitable medium under conditions conducive to production of a steviol glycoside, and, optionally, recovering the steviol glycoside.

8. The nucleic acid sequence of claim 1, encoding a polypeptide having UGT74G1 activity, wherein said polypeptide has:
 (i) a valine at position 35;
 (ii) an alanine at position 189;
 (iii) an asparagine at position 280;
 (iv) an asparagine at position 284;
 (v) a glycine at position 285;
 (vi) an asparagine at position 285;
 (vii) a serine at position 285;
 (viii) an alanine at position 334; and/or
 (ix) an alanine at position 373; said positions being defined with reference to SEQ ID NO:2.

9. The nucleic acid sequence of claim 1, wherein the amino acid sequence encoded has at least 95% sequence identity with SEQ ID NO:2.

10. The nucleic acid sequence of claim 1, wherein the amino acid sequence encoded has at least 90% sequence identity with a sequence selected from the group consisting of SEQ ID NOs: 4, 6, 8, 10, 12, 14, 16, 18, and 20.

* * * * *

SEQUENCE LISTING

<160> NUMBER OF SEQ ID NOS: 34

<210> SEQ ID NO 1
<211> LENGTH: 1383
<212> TYPE: DNA
<213> ORGANISM: Stevia rebaudiana

<400> SEQUENCE: 1

```
atggccgagc agcagaagat caagaagtct ccccacgttc tgctcatccc cttccctctg     60
cagggccaca tcaaccccct catccagttc ggcaagcgac tcatctccaa gggtgtcaag    120
accactctgg tcaccaccat ccacaccctc aactccactc tcaaccactc caacaccacc    180
accacctcca tcgagatcca ggccatctcc gacggctgtg acgagggtgg tttcatgtct    240
gctggtgagt cttacctcga gactttcaag caggtcggtt ccaagtctct ggctgacctc    300
atcaagaagc tccagtccga gggtaccacc attgacgcca tcatctacga ctccatgacc    360
gagtgggttc tcgatgtcgc catcgagttt ggtattgacg tggctccttt cttcacccag    420
gcctgtgtcg tcaactctct ctactaccac gtccacaagg gtctgatctc tctgcccctc    480
ggcgagactg tctccgtccc cggtttcccc gttctgcagc gatgggagac tcctctcatt    540
ctccagaacc acgagcagat ccagtccccc tggtcccaga tgctcttcgg ccagttcgcc    600
aacattgacc aggcccgatg ggttttcacc aactccttct acaagctcga ggaagaggtc    660
attgagtgga cccgaaagat ctggaacctc aaggtcattg gccccaccct ccctccatg     720 tacctcgaca gcgactcga tgacgacaag gacaacggtt tcaacctcta caaggccaac    780
caccacgagt gcatgaactg gctcgacgac aagcccaagg agtccgttgt ctacgttgcc    840
tttggctctc tggtcaagca cggccccgag caggttgagg agatcaccg agctctgatt    900 gactccgatg tcaacttcct gtgggtcatc aagcacaagg aagagggtaa gctccccgag    960
aacctgtccg aggtcatcaa gaccggcaag ggcctcattg ttgcctggtg caagcagctc   1020
gacgttctcg cccacgagtc cgtcggctgc tttgtcaccc actgcggttt caactccacc   1080
ctcgaggcta tctctctcgg tgtccccgtt gttgccatgc cccagttctc cgaccagacc   1140
accaacgcca agctcctcga tgagattctc ggtgtcggtg tccgagtcaa ggctgacgag   1200
aacggtattg tccgacgagg taacctggct tcttgtatca agatgatcat ggaggaagag   1260
```

```
cgaggtgtca tcatccgaaa gaacgccgtc aagtggaagg atctggccaa ggttgctgtc    1320
cacgagggtg gctcttccga caacgacatt gtcgagtttg tctccgagct catcaaggcc    1380
taa                                                                  1383
```

<210> SEQ ID NO 2
<211> LENGTH: 460
<212> TYPE: PRT
<213> ORGANISM: Stevia rebaudiana

<400> SEQUENCE: 2

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
```

```
              340             345             350
Thr His Cys Gly Phe Asn Ser Thr Leu Glu Ala Ile Ser Leu Gly Val
        355                 360                 365

Pro Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 3
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 3
atggccgagc agcagaagat caagaagtct ccccacgttc tgctcatccc cttccctctg      60
cagggccaca tcaaccccct tcatccagtt ggcaagcgac tcgtctccaa gggtgtcaag     120
accactctgg tcaccaccat ccacaccctc aactccactc tcaaccactc caacaccacc     180
accacctcca tcgagatcca ggccatctcc gacggctgtg acgagggtgg tttcatgtct     240
gctggtgagt cttacctcga ctttcaag caggtcggtt ccaagtctct ggctgaccct      300
atcaagaagc tccagtccga gggtaccacc attgacgcca tcatctacga ctccatgacc     360
gagtgggttc tcgatgtcgc catcgagttt ggtattgacg tggctccctt cttcacccag     420
gcctgtgtcg tcaactctct ctactaccac gtccacaagg tctgatctc tgcccctc      480 ggcgagactg tctccgtccc cggtttcccc gttctgcagc gatgggagac tcctctcatt     540
ctccagaacc acgagcagat ccagtccccc tggtcccaga tgctcttcgg ccagttcgcc     600
aacattgacc aggcccgatg ggttttcacc aactccttct acaagctcga ggaagaggtc     660
attgagtgga cccgaaagat ctggaaccctc aaggtcattg gccccacccct ccctccatg     720 tacctcgaca gcgactcga tgacgacaag gacaacggtt caacctctcta caaggccaac     780 caccacgagt gcatgaactg gctcgacgac aagcccaagg agtccgttgt ctacgttgcc     840
tttggctctc tggtcaagca cggccccgag caggttgagg agatcacccg agctctgatt     900
gactccgatg tcaacttcct gtgggtcatc aagcacaagg aagagggtaa gctccccgag     960
aacctgtccg aggtcatcaa gaccggcaag ggcctcattg ttgcctggtg caagcagctc    1020
gacgttctcg cccacgagtc cgtcggctgc tttgtcaccc actgcggttt caactccacc    1080
ctcgaggcta tctctctcgg tgtccccgtt gttgccatgc cccagttctc cgaccagacc    1140
accaacgcca agctcctcga tgagattctc ggtgtcggtg tccgagtcaa ggctgacgag    1200
aacggtattg tccgacgagg taacctggct tcttgtatca agatgatcat ggaggaagag    1260
cgaggtgtca tcatccgaaa gaacgccgtc aagtggaagg atctggccaa ggttgctgtc    1320
cacgagggtg gctcttccga caacgacatt gtcgagtttg tctccgagct catcaaggcc    1380
``` taa                                                               1383

<210> SEQ ID NO 4
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 4

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Val Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Asp Asn Gly Phe Asn Leu
                245                 250                 255

Tyr Lys Ala Asn His His Glu Cys Met Asn Trp Leu Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350
```

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
        370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
        450                 455                 460

<210> SEQ ID NO 5
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 5
atggccgagc agcagaagat caagaagtct ccccacgttc tgctcatccc cttccctctg        60
cagggccaca tcaaccccct tcatccagtt ggcaagcgac tcatctccaa gggtgtcaag       120
accactctgg tcaccaccat ccacaccctc aactccactc tcaaccactc caacaccacc       180
accacctcca tcgagatcca ggccatctcc gacggctgtg acgagggtgg tttcatgtct       240
gctggtgagt cttacctcga gactttcaag caggtcggtt ccagtctctc tggctgacctc      300 atcaagaagc tccagtccga gggtaccacc attgacgcca tcatctacga ctccatgacc       360
gagtgggttc tcgatgtcgc catcgagttt ggtattgacg tggctccctt cttcacccag       420
gcctgtgtcg tcaactctct ctactaccac gtccacaagg gtctgatctc tctgcccctc       480
ggcgagactg tctccgtccc cggtttcccc gttctgcagc gatgggagac tcctctcatt       540
ctccagaacc acgagcagat ccaggccccc tggtcccaga tgctcttcgg ccagttcgcc       600
aacattgacc aggcccgatg ggttttcacc aactccttct acaagctcga ggaagaggtc       660
attgagtgga cccgaaagat ctggaacctc aaggtcattg gccccaccct cccctccatg       720
tacctcgaca gcgactcga tgacgacaag gacaacggtt caacctctca aggccaac         780 caccacgagt gcatgaactg gctcgacgac aagcccaagg agtccgttgt ctacgttgcc       840
tttggctctc tggtcaagca cggccccgag caggttgagg agatcacccg agctctgatt       900
gactccgatg tcaacttcct gtgggtcatc aagcacaagg aagagggtaa gctccccgag       960
aacctgtccg aggtcatcaa gaccggcaag ggcctcattg ttgcctggtg caagcagctc      1020
gacgttctcg cccacgagtc cgtcggctgc tttgtcaccc actgcggttt caactccacc      1080
ctcgaggcta tctctctcgg tgtccccgtt gttgccatgc ccagttctcc gaccagacc       1140 accaacgcca agtccctcga tgagattctc ggtgtcggtg tccgagtcaa ggctgacgag      1200
aacggtattg tccgacgagg taacctggct tcttgtatca agatgatcat ggaggaagag      1260
cgaggtgtca tcatccgaaa gaacgccgtc aagtggaagg atctggccaa ggttgctgtc      1320
cacgagggtg gctcttccga caacgacatt gtcgagtttg tctccgagct catcaaggcc      1380
taa                                                                   1383

```
<210> SEQ ID NO 6
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 6
```

| | | | | | | | | | | | | | | |
|---|---|---|---|---|---|---|---|---|---|---|---|---|---|---|
| Met | Ala | Glu | Gln | Gln | Lys | Ile | Lys | Lys | Ser | Pro | His | Val | Leu | Ile |
| 1 | | | | 5 | | | | | 10 | | | | | 15 |
| Pro | Phe | Pro | Leu | Gln | Gly | His | Ile | Asn | Pro | Phe | Ile | Gln | Phe | Gly | Lys |
| | | | 20 | | | | | 25 | | | | | 30 | | |
| Arg | Leu | Ile | Ser | Lys | Gly | Val | Lys | Thr | Thr | Leu | Val | Thr | Thr | Ile | His |
| | | | 35 | | | | | 40 | | | | | 45 | | |
| Thr | Leu | Asn | Ser | Thr | Leu | Asn | His | Ser | Asn | Thr | Thr | Thr | Thr | Ser | Ile |
| | 50 | | | | | 55 | | | | | 60 | | | | |
| Glu | Ile | Gln | Ala | Ile | Ser | Asp | Gly | Cys | Asp | Glu | Gly | Gly | Phe | Met | Ser |
| 65 | | | | | 70 | | | | | 75 | | | | | 80 |
| Ala | Gly | Glu | Ser | Tyr | Leu | Glu | Thr | Phe | Lys | Gln | Val | Gly | Ser | Lys | Ser |
| | | | | 85 | | | | | 90 | | | | | 95 | |
| Leu | Ala | Asp | Leu | Ile | Lys | Lys | Leu | Gln | Ser | Glu | Gly | Thr | Thr | Ile | Asp |
| | | | 100 | | | | | 105 | | | | | 110 | | |
| Ala | Ile | Ile | Tyr | Asp | Ser | Met | Thr | Glu | Trp | Val | Leu | Asp | Val | Ala | Ile |
| | | | 115 | | | | | 120 | | | | | 125 | | |
| Glu | Phe | Gly | Ile | Asp | Gly | Gly | Ser | Phe | Phe | Thr | Gln | Ala | Cys | Val | Val |
| | 130 | | | | | 135 | | | | | 140 | | | | |
| Asn | Ser | Leu | Tyr | Tyr | His | Val | His | Lys | Gly | Leu | Ile | Ser | Leu | Pro | Leu |
| 145 | | | | | 150 | | | | | 155 | | | | | 160 |
| Gly | Glu | Thr | Val | Ser | Val | Pro | Gly | Phe | Pro | Val | Leu | Gln | Arg | Trp | Glu |
| | | | | 165 | | | | | 170 | | | | | 175 | |
| Thr | Pro | Leu | Ile | Leu | Gln | Asn | His | Glu | Gln | Ile | Gln | Ala | Pro | Trp | Ser |
| | | | 180 | | | | | 185 | | | | | 190 | | |
| Gln | Met | Leu | Phe | Gly | Gln | Phe | Ala | Asn | Ile | Asp | Gln | Ala | Arg | Trp | Val |
| | | | 195 | | | | | 200 | | | | | 205 | | |
| Phe | Thr | Asn | Ser | Phe | Tyr | Lys | Leu | Glu | Glu | Glu | Val | Ile | Glu | Trp | Thr |
| | 210 | | | | | 215 | | | | | 220 | | | | |
| Arg | Lys | Ile | Trp | Asn | Leu | Lys | Val | Ile | Gly | Pro | Thr | Leu | Pro | Ser | Met |
| 225 | | | | | 230 | | | | | 235 | | | | | 240 |
| Tyr | Leu | Asp | Lys | Arg | Leu | Asp | Asp | Lys | Asp | Asn | Gly | Phe | Asn | Leu |
| | | | | 245 | | | | | 250 | | | | | 255 |
| Tyr | Lys | Ala | Asn | His | His | Glu | Cys | Met | Asn | Trp | Leu | Asp | Asp | Lys | Pro |
| | | | 260 | | | | | 265 | | | | | 270 | | |
| Lys | Glu | Ser | Val | Val | Tyr | Val | Ala | Phe | Gly | Ser | Leu | Val | Lys | His | Gly |
| | | | 275 | | | | | 280 | | | | | 285 | | |
| Pro | Glu | Gln | Val | Glu | Glu | Ile | Thr | Arg | Ala | Leu | Ile | Asp | Ser | Asp | Val |
| | 290 | | | | | 295 | | | | | 300 | | | | |
| Asn | Phe | Leu | Trp | Val | Ile | Lys | His | Lys | Glu | Glu | Gly | Lys | Leu | Pro | Glu |
| 305 | | | | | 310 | | | | | 315 | | | | | 320 |
| Asn | Leu | Ser | Glu | Val | Ile | Lys | Thr | Gly | Lys | Gly | Leu | Ile | Val | Ala | Trp |
| | | | | 325 | | | | | 330 | | | | | 335 | |
| Cys | Lys | Gln | Leu | Asp | Val | Leu | Ala | His | Glu | Ser | Val | Gly | Cys | Phe | Val |
| | | | 340 | | | | | 345 | | | | | 350 | | |
| Thr | His | Cys | Gly | Phe | Asn | Ser | Thr | Leu | Glu | Ala | Ile | Ser | Leu | Gly | Val |
| | | | 355 | | | | | 360 | | | | | 365 | | |

```
Pro Val Val Ala Met Pro Gln Phe Ser Asp Gln Thr Thr Asn Ala Lys
        370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
            450                 455                 460

<210> SEQ ID NO 7
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 7
```

| | | |
|---|---|---|
| atggccgagc agcagaagat caagaagtct ccccacgttc tgctcatccc cttccctctg | 60 |
| cagggccaca tcaaccccct tcatccagtt cggcaagcga ctcatctcca gggtgtcaag | 120 |
| accactctgg tcaccaccat ccacacccte aactccactc tcaaccactc caacaccacc | 180 |
| accacctcca tcgagatcca ggccatctcc gacggctgtg acgagggtgg tttcatgtct | 240 |
| gctggtgagt cttacctcga ctttcaag caggtcggtt ccaagtctct ggctgaccte | 300 |
| atcaagaagc tccagtccga gggtaccacc attgacgcca tcatctacga ctccatgacc | 360 |
| gagtgggttc tcgatgtcgc catcgagttt ggtattgacg tggctccett cttcacccag | 420 |
| gcctgtgtcg tcaactctct ctactaccac gtccacaagg tctgatctc tctgcccctc | 480 |
| ggcgagactg tctccgtccc cggtttcccc gttctgcagc gatgggagac tcctctcatt | 540 |
| ctccagaacc acgagcagat ccagtccccc tggtcccaga tgctcttcgg ccagttcgcc | 600 |
| aacattgacc aggcccgatg gttttcacc aactccttct acaagctcga ggaagaggtc | 660 |
| attgagtgga cccgaaagat ctggaaccte aaggtcattg cccccacccct cccctccatg | 720 |
| tacctcgaca gcgactcga tgacgacaag gacaacggtt tcaacctcta caggccaac | 780 |
| caccacgagt gcatgaactg gctcgacgac aagcccaagg agtccgttgt ctacgttaac | 840 |
| tttggctctc tggtcaagca cggccccgag caggttgagg agatcacccg agctctgatt | 900 |
| gactccgatg tcaacttcct gtgggtcatc aagcacaagg aagagggtaa gctccccgag | 960 |
| aacctgtccg aggtcatcaa gaccggcaag ggcctcattg ttgcctggtg caagcagctc | 1020 |
| gacgttctcg cccacgagtc cgtcggctgc tttgtcaccc actgcggttt caactccacc | 1080 |
| ctcgaggcta tctctctcgg tgtccccgtt gttgccatgc cccagttctc cgaccagacc | 1140 |
| accaacgcca agctcctcga tgagattctc ggtgtcggtg tccgagtcaa ggctgacgag | 1200 |
| aacggtattg tccgacgagg taacctggct tcttgtatca agatgatcat ggaggaagag | 1260 |
| cgaggtgtca tcatccgaaa gaacgccgtc aagtggaagg atctggccaa ggttgctgtc | 1320 |
| cacgagggtg gctcttccga caacgacatt gtcgagtttg tctccgagct catcaaggcc | 1380 |
| taa | 1383 |

<210> SEQ ID NO 8
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 8

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Asn Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
```

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
            450                 455                 460

<210> SEQ ID NO 9
<211> LENGTH: 1383
<212> TYPE: DNA
<213> ORGANISM: Artificial sequence
<220> FEATURE:
<223> OTHER INFORMATION: UDP-glycosyltransferase variant encoding sequence

<400> SEQUENCE: 9

```
atggccgagc agcagaagat caagaagtct ccccacgttc tgctcatccc cttccctctg        60
cagggccaca tcaaccccct catccagttc ggcaagcgac tcatctccaa gggtgtcaag       120
accactctgg tcaccaccat ccacaccctc aactccactc tcaaccactc caacaccacc       180
accacctcca tcgagatcca ggccatctcc gacggctgtg acgagggtgg tttcatgtct       240
gctggtgagt cttacctcga cttttcaag caggtcggtt ccagtctct ggctgacctc         300
atcaagaagc tccagtccga gggtaccacc attgacgcca tcatctacga ctccatgacc       360
gagtgggttc tcgatgtcgc catcgagttt ggtattgacg tggctccctt cttcacccag       420
gcctgtgtcg tcaactctct ctactaccac gtccacaagg tctgatctc tctgcccctc        480
ggcgagactg tctccgtccc cggtttcccc gttctgcagc gatgggagac tcctctcatt       540
ctccagaacc acgagcagat ccagtccccc tggtcccaga tgctcttcgg ccagttcgcc       600
aacattgacc aggcccgatg ggttttcacc aactccttct acaagctcga ggaagaggtc       660
attgagtgga cccgaaagat ctggaacctc aaggtcattg gccccaccct ccctccatg        720
tacctcgaca gcgactcga tgacgacaag gacaacggtt tcaacctcta caaggccaac       780
caccacgagt gcatgaactg gctcgacgac aagcccaagg agtccgttgt ctacgttgcc       840
tttggctcta acgtcaagca cggccccgag caggttgagg agatcacccg agctctgatt       900
gactccgatg tcaacttcct gtgggtcatc aagcacaagg aagagggtaa gctccccgag       960
aacctgtccg aggtcatcaa gaccggcaag ggcctcattg ttgcctggtg caagcagctc      1020
gacgttctcg cccacgagtc cgtcggctgc tttgtcaccc actgcggttt caactccacc      1080
ctcgaggcta tctctctcgg tgtccccgtt gttgccatgc ccagttctc cgaccagacc       1140
accaacgcca agctcctcga tgagattctc ggtgtcggtg tccgagtcaa ggctgacgag      1200
aacggtattg tccgacgagg taacctggct tcttgtatca agatgatcat ggaggaagag      1260
cgaggtgtca tcatccgaaa gaacgccgtc aagtggaagg atctggccaa ggttgctgtc      1320
cacgagggtg gctcttccga caacgacatt gtcgagtttg tctccgagct catcaaggcc      1380
taa                                                                    1383
```

<210> SEQ ID NO 10
<211> LENGTH: 460

<212> TYPE: PRT
<213> ORGANISM: Artificial sequence
<220> FEATURE:
<223> OTHER INFORMATION: UDP-glycosyltransferase variant

<400> SEQUENCE: 10

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Asn Val Lys His Gly
        275                 280                 285

Pro Glu Gln Val Glu Glu Ile Thr Arg Ala Leu Ile Asp Ser Asp Val
290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
370                 375                 380
```

```
Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
        420                 425                 430

Lys Asp Leu Ala Lys Val Ala Val His Glu Gly Gly Ser Ser Asp Asn
    435                 440                 445

Asp Ile Val Glu Phe Val Ser Glu Leu Ile Lys Ala
    450                 455                 460

<210> SEQ ID NO 11
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 11
atggccgagc agcagaagat caagaagtct ccccacgttc tgctcatccc cttccctctg      60
cagggccaca tcaaccccct tcatccagtt ggcaagcgac tcatctccaa gggtgtcaag     120
accactctgg tcaccaccat ccacaccctc aactccactc tcaaccactc caacaccacc     180
accacctcca tcgagatcca ggccatctcc gacggctgtg acgagggtgg tttcatgtct     240
gctggtgagt cttacctcga ctttcaag caggtcggtt ccaagtctct ggctgacctc      300
atcaagaagc tccagtccga gggtaccacc attgacgcca tcatctacga ctccatgacc     360
gagtgggttc tcgatgtcgc catcgagttt ggtattgacg gtggctcctt cttcacccag     420
gcctgtgtcg tcaactctct ctactaccac gtccacaagg tctgatctc tctgccctc      480 ggcgagactg tctccgtccc cggtttcccc gttctgcagc gatgggagac tcctctcatt     540
ctccagaacc acgagcagat ccagtccccc tggtcccaga tgctcttcgg ccagttcgcc     600
aacattgacc aggcccgatg ggttttcacc aactccttct acaagctcga ggaagaggtc     660
attgagtgga cccgaaagat ctggaacctc aaggtcattg cccccaccct ccctccatg      720 tacctcgaca gcgactcga tgacgacaag acaacggtt tcaacctcta caggccaac       780 caccacgagt gcatgaactg gctcgacgac aagcccaagg agtccgttgt ctacgttgcc     840
tttggctctc tgggcaagca cggccccgag caggttgagg agatcacccg agctctgatt     900
gactccgatg tcaacttcct gtgggtcatc aagcacaagg aagagggtaa gctccccgag     960
aacctgtccg aggtcatcaa gaccggcaag ggcctcattg ttgcctggtg caagcagctc    1020
gacgttctcg cccacgagtc cgtcggctgc tttgtcaccc actgcggttt caactccacc    1080
ctcgaggcta tctctctcgg tgtccccgtt gttgccatgc ccagttctc cgaccagacc      1140 accaacgcca agctcctcga tgagattctc ggtgtcggtg tccgagtcaa ggctgacgag    1200
aacggtattg tccgacgagg taacctggct tcttgtatca agatgatcat ggaggaagag    1260
cgaggtgtca tcatccgaaa gaacgccgtc aagtggaagg atctggccaa ggttgctgtc    1320
cacgagggtg gctcttccga caacgacatt gtcgagtttg tctccgagct catcaaggcc    1380
taa                                                                   1383

<210> SEQ ID NO 12
<211> LENGTH: 460
<212> TYPE: PRT
<213> ORGANISM: Artificial sequence
```

<220> FEATURE:
<223> OTHER INFORMATION: UDP-glycosyltransferase variant

<400> SEQUENCE: 12

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Gly Lys His Gly
        275                 280                 285

Pro Glu Gln Val Glu Glu Ile Thr Arg Ala Leu Ile Asp Ser Asp Val
290                 295                 300

Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400
```

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
        420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 13
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 13

| | |
|---|---|
| atggccgagc agcagaagat caagaagtct ccccacgttc tgctcatccc cttccctctg | 60 |
| cagggccaca tcaaccccct catccagttc ggcaagcgac tcatctccaa gggtgtcaag | 120 |
| accactctgg tcaccaccat ccacaccctc aactccactc tcaaccactc caacaccacc | 180 |
| accacctcca tcgagatcca ggccatctcc gacggctgtg acgagggtgg tttcatgtct | 240 |
| gctggtgagt cttacctcga gactttcaag caggtcggtt ccagtctctc ggctgacctc | 300 |
| atcaagaagc tccagtccga gggtaccacc attgacgcca tcatctacga ctccatgacc | 360 |
| gagtgggttc tcgatgtcgc catcgagttt ggtattgacg tggctccctt cttcacccag | 420 |
| gcctgtgtcg tcaactctct ctactaccac gtccacaagg gtctgatctc tctgcccctc | 480 |
| ggcgagactg tctccgtccc cggtttcccc gttctgcagc gatgggagac tcctctcatt | 540 |
| ctccagaacc acgagcagat ccagtccccc tggtcccaga tgctcttcgg ccagttcgcc | 600 |
| aacattgacc aggcccgatg ggttttcacc aactccttct acaagctcga ggaagaggtc | 660 |
| attgagtgga cccgaaagat ctggaacctc aaggtcattg gccccaccct ccctccatg | 720 |
| tacctcgaca gcgactcga tgacgacaag gacaacggtt tcaacctcta caaggccaac | 780 |
| caccacgagt gcatgaactg gctcgacgac aagcccaagg agtccgttgt ctacgttgcc | 840 |
| tttggctctc tgaacaagca cggccccgag caggttgagg agatcacccg agctctgatt | 900 |
| gactccgatg tcaacttcct gtgggtcatc aagcacaagg aagagggtaa gctccccgag | 960 |
| aacctgtccg aggtcatcaa gaccggcaag ggcctcattg ttgcctggtg caagcagctc | 1020 |
| gacgttctcg cccacgagtc cgtcggctgc tttgtcaccc actgcggttt caactccacc | 1080 |
| ctcgaggcta tctctctcgg tgtccccgtt gttgccatgc cccagttctc cgaccagacc | 1140 |
| accaacgcca agctcctcga tgagattctc ggtgtcggtg tccgagtcaa ggctgacgag | 1200 |
| aacggtattg tccgacgagg taacctggct tcttgtatca agatgatcat ggaggaagag | 1260 |
| cgaggtgtca tcatccgaaa gaacgccgtc aagtggaagg atctggccaa ggttgctgtc | 1320 |
| cacgagggtg gctcttccga caacgacatt gtcgagtttg tctccgagct catcaaggcc | 1380 |
| taa | 1383 |

<210> SEQ ID NO 14
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 14

```
Met Ala Glu Gln Gln Lys Ile Lys Lys Ser Pro His Val Leu Leu Ile
1               5                   10                  15
Pro Phe Pro Leu Gln Gly His Ile Asn Pro Phe Ile Gln Phe Gly Lys
                20                  25                  30
Arg Leu Ile Ser Lys Gly Val Lys Thr Thr Leu Val Thr Thr Ile His
            35                  40                  45
Thr Leu Asn Ser Thr Leu Asn His Ser Asn Thr Thr Thr Thr Ser Ile
        50                  55                  60
Glu Ile Gln Ala Ile Ser Asp Gly Cys Asp Glu Gly Gly Phe Met Ser
65                  70                  75                  80
Ala Gly Glu Ser Tyr Leu Glu Thr Phe Lys Gln Val Gly Ser Lys Ser
                85                  90                  95
Leu Ala Asp Leu Ile Lys Lys Leu Gln Ser Glu Gly Thr Thr Ile Asp
            100                 105                 110
Ala Ile Ile Tyr Asp Ser Met Thr Glu Trp Val Leu Asp Val Ala Ile
        115                 120                 125
Glu Phe Gly Ile Asp Gly Gly Ser Phe Phe Thr Gln Ala Cys Val Val
130                 135                 140
Asn Ser Leu Tyr Tyr His Val His Lys Gly Leu Ile Ser Leu Pro Leu
145                 150                 155                 160
Gly Glu Thr Val Ser Val Pro Gly Phe Pro Val Leu Gln Arg Trp Glu
                165                 170                 175
Thr Pro Leu Ile Leu Gln Asn His Glu Gln Ile Gln Ser Pro Trp Ser
            180                 185                 190
Gln Met Leu Phe Gly Gln Phe Ala Asn Ile Asp Gln Ala Arg Trp Val
        195                 200                 205
Phe Thr Asn Ser Phe Tyr Lys Leu Glu Glu Glu Val Ile Glu Trp Thr
210                 215                 220
Arg Lys Ile Trp Asn Leu Lys Val Ile Gly Pro Thr Leu Pro Ser Met
225                 230                 235                 240
Tyr Leu Asp Lys Arg Leu Asp Asp Lys Asp Asn Gly Phe Asn Leu
                245                 250                 255
Tyr Lys Ala Asn His His Glu Cys Met Asn Trp Leu Asp Asp Lys Pro
            260                 265                 270
Lys Glu Ser Val Val Tyr Val Ala Phe Gly Ser Leu Asn Lys His Gly
        275                 280                 285
Pro Glu Gln Val Glu Glu Ile Thr Arg Ala Leu Ile Asp Ser Asp Val
290                 295                 300
Asn Phe Leu Trp Val Ile Lys His Lys Glu Glu Gly Lys Leu Pro Glu
305                 310                 315                 320
Asn Leu Ser Glu Val Ile Lys Thr Gly Lys Gly Leu Ile Val Ala Trp
                325                 330                 335
Cys Lys Gln Leu Asp Val Leu Ala His Glu Ser Val Gly Cys Phe Val
            340                 345                 350
Thr His Cys Gly Phe Asn Ser Thr Leu Glu Ala Ile Ser Leu Gly Val
        355                 360                 365
Pro Val Val Ala Met Pro Gln Phe Ser Asp Gln Thr Thr Asn Ala Lys
370                 375                 380
Leu Leu Asp Glu Ile Leu Gly Val Gly Val Arg Val Lys Ala Asp Glu
385                 390                 395                 400
Asn Gly Ile Val Arg Arg Gly Asn Leu Ala Ser Cys Ile Lys Met Ile
```

Met Glu Glu Glu Arg Gly Val Ile Ile Arg Lys Asn Ala Val Lys Trp
                    420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 15
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 15

| | | | | | |
|---|---|---|---|---|---|
| atggccgagc | agcagaagat | caagaagtct | ccccacgttc | tgctcatccc | cttccctctg | 60 |
| cagggccaca | tcaacccctt | catccagttc | ggcaagcgac | tcatctccaa | gggtgtcaag | 120 |
| accactctgg | tcaccaccat | ccacaccctc | aactccactc | tcaaccactc | caacaccacc | 180 |
| accacctcca | tcgagatcca | ggccatctcc | gacggctgtg | acgagggtgg | tttcatgtct | 240 |
| gctggtgagt | cttacctcga | gactttcaag | caggtcggtt | ccaagtctct | ggctgacctc | 300 |
| atcaagaagc | tccagtccga | gggtaccacc | attgacgcca | tcatctacga | ctccatgacc | 360 |
| gagtgggttc | tcgatgtcgc | catcgagttt | ggtattgacg | tggctccttc | ttcacccag | 420 |
| gcctgtgtcg | tcaactctct | ctactaccac | gtccacaagg | tctgatctc | tctgcccctc | 480 |
| ggcgagactg | tctccgtccc | cggtttcccc | gttctgcagc | gatgggagac | tcctctcatt | 540 |
| ctccagaacc | acgagcagat | ccagtccccc | tggtcccaga | tgctcttcgg | ccagttcgcc | 600 |
| aacattgacc | aggcccgatg | ggttttcacc | aactccttct | acaagctcga | ggaagaggtc | 660 |
| attgagtgga | cccgaaagat | ctggaacctc | aaggtcattg | ccccacccct | cccctccatg | 720 |
| tacctcgaca | gcgactcga | tgacgacaag | gacaacggtt | tcaacctcta | caaggccaac | 780 |
| caccacgagt | gcatgaactg | gctcgacgac | aagcccaagg | agtccgttgt | ctacgttgcc | 840 |
| tttggctctc | tgtccaagca | cggccccgag | caggttgagg | agatcacccg | agctctgatt | 900 |
| gactccgatg | tcaacttcct | gtgggtcatc | aagcacaagg | aagagggtaa | gctccccgag | 960 |
| aacctgtccg | aggtcatcaa | gaccggcaag | ggcctcattg | ttgcctggtg | caagcagctc | 1020 |
| gacgttctcg | cccacgagtc | cgtcggctgc | tttgtcaccc | actgcggttt | caactccacc | 1080 |
| ctcgaggcta | tctctctcgg | tgtccccgtt | gttgccatgc | cccagttctc | cgaccagacc | 1140 |
| accaacgcca | agctcctcga | tgagattctc | ggtgtcggtg | tccgagtcaa | ggctgacgag | 1200 |
| aacggtattg | tccgacgagg | taacctggct | tcttgtatca | agatgatcat | ggaggaagag | 1260 |
| cgaggtgtca | tcatccgaaa | gaacgccgtc | aagtggaagg | atctggccaa | ggttgctgtc | 1320 |
| cacgagggtg | gctcttccga | caacgacatt | gtcgagtttg | tctccgagct | catcaaggcc | 1380 |
| taa | | | | | | 1383 |

<210> SEQ ID NO 16
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 16

-continued

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Ser Lys His Gly
        275                 280                 285

Pro Glu Gln Val Glu Glu Ile Thr Arg Ala Leu Ile Asp Ser Asp Val
290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415
```

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 17
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 17

| | |
|---|---|
| atggccgagc agcagaagat caagaagtct ccccacgttc tgctcatccc cttccctctg | 60 |
| cagggccaca tcaaccccct catccagttc ggcaagcgac tcatctccaa gggtgtcaag | 120 |
| accactctgg tcaccaccat ccacaccctc aactccactc tcaaccactc caacaccacc | 180 |
| accacctcca tcgagatcca ggccatctcc gacggctgtg acgagggtgg tttcatgtct | 240 |
| gctggtgagt cttacctcga gactttcaag caggtcggtt ccagtctct ggctgacctc | 300 |
| atcaagaagc tccagtccga gggtaccacc attgacgcca tcatctacga ctccatgacc | 360 |
| gagtgggttc tcgatgtcgc catcgagttt ggtattgacg tggctccctt cttcacccag | 420 |
| gcctgtgtcg tcaactctct ctactaccac gtccacaagg gtctgatctc tctgcccctc | 480 |
| ggcgagactg tctccgtccc cggtttcccc gttctgcagc gatgggagac tcctctcatt | 540 |
| ctccagaacc acgagcagat ccagtccccc tggtcccaga tgctcttcgg ccagttcgcc | 600 |
| aacattgacc aggcccgatg ggttttcacc aactccttct acaagctcga ggaagaggtc | 660 |
| attgagtgga cccgaaagat ctggaacctc aaggtcattg gccccaccct cccctccatg | 720 |
| tacctcgaca gcgactcga tgacgacaag gacaacggtt caacctcta caaggccaac | 780 |
| caccacgagt gcatgaactg gctcgacgac aagcccaagg agtccgttgt ctacgttgcc | 840 |
| tttggctctc tggtcaagca cggccccgag caggttgagg agatcacccg agctctgatt | 900 |
| gactccgatg tcaacttcct gtgggtcatc aagcacaagg aagagggtaa gctccccgag | 960 |
| aacctgtccg aggtcatcaa gaccggcaag ggcctcattg ctgcctggtg caagcagctc | 1020 |
| gacgttctcg cccacgagtc cgtcggctgc tttgtcaccc actgcggttt caactccacc | 1080 |
| ctcgaggcta tctctctcgg tgtccccgtt gttgccatgc cccagttctc cgaccagacc | 1140 |
| accaacgcca agctcctcga tgagattctc ggtgtcggtg tccgagtcaa ggctgacgag | 1200 |
| aacggtattg tccgacgagg taacctggct tcttgtatca agatgatcat ggaggaagag | 1260 |
| cgaggtgtca tcatccgaaa gaacgccgtc aagtggaagg atctggccaa ggttgctgtc | 1320 |
| cacgagggtg gctcttccga caacgacatt gtcgagtttg tctccgagct catcaaggcc | 1380 |
| taa | 1383 |

<210> SEQ ID NO 18
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 18

Met Ala Glu Gln Gln Lys Ile Lys Lys Ser Pro His Val Leu Leu Ile

-continued

```
1               5                   10                  15
Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
            50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                    85                  90                  95

Leu Ala Asp Leu Ile Lys Lys Leu Gln Ser Glu Gly Thr Thr Ile Asp
                100                 105                 110

Ala Ile Ile Tyr Asp Ser Met Thr Glu Trp Val Leu Asp Val Ala Ile
                115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                    165                 170                 175

Thr Pro Leu Ile Leu Gln Asn His Glu Gln Ile Gln Ser Pro Trp Ser
                180                 185                 190

Gln Met Leu Phe Gly Gln Phe Ala Asn Ile Asp Gln Ala Arg Trp Val
                195                 200                 205

Phe Thr Asn Ser Phe Tyr Lys Leu Glu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                    245                 250                 255

Tyr Lys Ala Asn His His Glu Cys Met Asn Trp Leu Asp Asp Lys Pro
                260                 265                 270

Lys Glu Ser Val Val Tyr Val Ala Phe Gly Ser Leu Val Lys His Gly
                275                 280                 285

Pro Glu Gln Val Glu Ile Thr Arg Ala Leu Ile Asp Ser Asp Val
                290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Ala Ala Trp
                    325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
                355                 360                 365

Pro Val Val Ala Met Pro Gln Phe Ser Asp Gln Thr Thr Asn Ala Lys
                370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                    405                 410                 415

Met Glu Glu Glu Arg Gly Val Ile Ile Arg Lys Asn Ala Val Lys Trp
                420                 425                 430
```

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
        450                 455             460

<210> SEQ ID NO 19
<211> LENGTH: 1383
<212> TYPE: DNA
<213> ORGANISM: Artificial sequence
<220> FEATURE:
<223> OTHER INFORMATION: UDP-glycosyltransferase variant encoding
      sequence

<400> SEQUENCE: 19

| | | |
|---|---|---|
| atggccgagc agcagaagat caagaagtct ccccacgttc tgctcatccc cttccctctg | 60 |
| cagggccaca tcaacccctt catccagttc ggcaagcgac tcatctccaa gggtgtcaag | 120 |
| accactctgg tcaccaccat ccacaccctc aactccactc tcaaccactc caacaccacc | 180 |
| accacctcca tcgagatcca ggccatctcc gacggctgtg acgagggtgg tttcatgtct | 240 |
| gctggtgagt cttacctcga cttttcaag caggtcggtt ccaagtctct ggctgacctc | 300 |
| atcaagaagc tccagtccga gggtaccacc attgacgcca tcatctacga ctccatgacc | 360 |
| gagtgggttc tcgatgtcgc catcgagttt ggtattgacg tggctccttc cttcacccag | 420 |
| gcctgtgtcg tcaactctct ctactaccac gtccacaagg tctgatctc tctgcccctc | 480 |
| ggcgagactg tctccgtccc cggtttcccc gttctgcagc gatgggagac tcctctcatt | 540 |
| ctccagaacc acgagcagat ccagtccccc tggtcccaga tgctcttcgg ccagttcgcc | 600 |
| aacattgacc aggcccgatg ggttttcacc aactccttct acaagctcga ggaagaggtc | 660 |
| attgagtgga cccgaaagat ctggaacctc aaggtcattg cccccacccct cccctccatg | 720 |
| tacctcgaca gcgactcga tgacgacaag acaacggtt caacctcta caggccaac | 780 |
| caccacgagt gcatgaactg gctcgacgac aagcccaagg agtccgttgt ctacgttgcc | 840 |
| tttggctctc tggtcaagca cggccccgag caggttgagg agatcacccg agctctgatt | 900 |
| gactccgatg tcaacttcct gtgggtcatc aagcacaagg aagagggtaa gctccccgag | 960 |
| aacctgtccg aggtcatcaa gaccggcaag ggcctcattg ttgcctggtg caagcagctc | 1020 |
| gacgttctcg cccacgagtc cgtcggctgc tttgtcaccc actgcggttt caactccacc | 1080 |
| ctcgaggcta tctctctcgg tgtccccgtt gttgccgccc ccagttctc cgaccagacc | 1140 |
| accaacgcca agctcctcga tgagattctc ggtgtcggtg tccgagtcaa ggctgacgag | 1200 |
| aacggtattg tccgacgagg taacctggct tcttgtatca agatgatcat ggaggaagag | 1260 |
| cgaggtgtca tcatccgaaa gaacgccgtc aagtggaagg atctggccaa ggttgctgtc | 1320 |
| cacgagggtg gctcttccga caacgacatt gtcgagtttg tctccgagct catcaaggcc | 1380 |
| taa | 1383 |

<210> SEQ ID NO 20
<211> LENGTH: 460
<212> TYPE: PRT
<213> ORGANISM: Artificial sequence
<220> FEATURE:
<223> OTHER INFORMATION: UDP-glycosyltransferase variant

<400> SEQUENCE: 20

Met Ala Glu Gln Gln Lys Ile Lys Lys Ser Pro His Val Leu Leu Ile
1               5                   10                  15

```
Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
            50                  55                  60

Glu Ile Gln Ala Ile Ser Asp Gly Cys Asp Glu Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
            130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
            165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
            195                 200                 205

Phe Thr Asn Ser Phe Tyr Lys Leu Glu Glu Val Ile Glu Trp Thr
            210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
            245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
            275                 280                 285

Pro Glu Gln Val Glu Glu Ile Thr Arg Ala Leu Ile Asp Ser Asp Val
            290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
            355                 360                 365

Pro Val Val Ala Ala Pro Gln Phe Ser Asp Gln Thr Thr Asn Ala Lys
            370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
```

435                 440                 445
Asp Ile Val Glu Phe Val Ser Glu Leu Ile Lys Ala
      450                 455                 460

<210> SEQ ID NO 21
<211> LENGTH: 1503
<212> TYPE: DNA
<213> ORGANISM: Artificial sequence
<220> FEATURE:
<223> OTHER INFORMATION: hydroxymethylglutaryl-CoA reductase from
      Yarrowia lipolitica, CpO for expression in Yarrowia lipolitica

<400> SEQUENCE: 21

```
atgacccagt ctgtgaaggt ggttgagaag cacgttccta tcgtcattga gaagcccagc      60
gagaaggagg aggacacctc ttctgaagac tccattgagc tgactgtcgg aaagcagccc     120
aagcccgtga ccgagacccg ttctctggac gacttggagg ctatcatgaa ggcaggtaag     180
accaagctcc tggaggacca cgaggttgtc aagctctctc tcgaaggcaa gctcccttTg     240
tatgctcttg agaagcagct tggtgacaac acccgagctt tggcatccg acgatctatc     300
atctcccagc agtctaatac caagactctt gagacctcaa agctccctta cctgcactac     360
gactacgacc gtgttttTgg agcctgttgc gagaacgtta ttggttacat gcctctcccc     420
gttggtgttg ctggccccat gaacattgat ggcaagaact accacattcc tatggccacc     480
actgagggtt gtcttgttgc ctcaaccatg cgaggttgca aggccatcaa cgccggtggc     540
ggtgttacca ctgtgcttac tcaggacggt atgacacgag tccttgtgt tccttcccc      600
tctctcaagc gggctggagc cgctaagatc tggcttgatt ccgaggaggg tctcaagtcc     660
atgcgaaagg ccttcaactc cacctctcga tttgctcgtc tccagtctct tcactctacc     720
cttgctggta acctgctgtt tattcgattc cgaaccacca ctggtgatgc catgggcatg     780
aacatgatct ccaagggcgt cgaacactct ctggccgtca tggtcaagga gtacggcttc     840
cctgatatgg acattgtgtc tgtctcgggt aactactgca ctgacaagaa gcccgcagcg     900
atcaactgga tcgaaggccg aggcaagagt gttgttgccg aagccaccat ccctgctcac     960
attgtcaagt ctgttctcaa agtgaggtt gacgctcttg ttgagctcaa catcagcaag    1020
aatctgatcg gtagtgccat ggctggctct gtgggaggtt tcaatgcaca cgccgcaaac    1080
ctggtgaccg ccatctacct tgccactggc caggatcctg ctcagaatgt cgagtcttcc    1140
aactgcatca cgctgatgag caacgtcgac ggtaacctgc tcatctccgt ttccatgcct    1200
tctatcgagg tcggtaccat tggtggaggt actattttgg agccccaggg tgctatgctg    1260
gagatgcttg gcgtgcgagg tcctcacatc gagaccccg gtgccaacgc caacagctt    1320
gctcgcatca ttgcttctgg agttcttgca gcggagcttt cgctgtgttc tgctcttgct    1380
gccggccatc ttgtgcaaag tcatatgacc cacaaccgtt cccaggctcc tactccggcc    1440
aagcagtctc aggccgatct gcagcgtctc caaaacggtt cgaatatctg cattcggtca    1500
tag                                                                  1503
```

<210> SEQ ID NO 22
<211> LENGTH: 984
<212> TYPE: DNA
<213> ORGANISM: Artificial sequence
<220> FEATURE:
<223> OTHER INFORMATION: Geranylgeranyl diphosphate synthase from
      Yarrowia lipolitica CpO for expression in Yarrowia lipolitica

<400> SEQUENCE: 22

```
atggattata acagcgcgga tttcaaggag atctggggca aggccgccga caccgcgctg      60
ctgggaccgt acaactacct cgccaacaac cggggccaca acatcagaga cacttgatc     120 gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttggagtcc cccaaaccat caactccgcc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg atggtggt gcacaagacc       480 ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtga                                            984
```

<210> SEQ ID NO 23
<211> LENGTH: 2232
<212> TYPE: DNA
<213> ORGANISM: Artificial sequence
<220> FEATURE:
<223> OTHER INFORMATION: Copalyl pyrophosphate synthase from Stevia rebaudiana CpO for expression in Yarrowia lipolitica

<400> SEQUENCE: 23

```
atgtgcaagg ctgttttccaa ggagtactcc gatctgctcc agaaggacga ggcctctttc      60
accaagtggg acgacgacaa ggtcaaggac cacctcgaca ccaacaagaa cctctacccc    120
aacgacgaga tcaaggagtt tgtcgagtcc gtcaaggcca tgttcggctc catgaacgac    180
ggcgagatta atgtctctgc ttacgacacc gcctggttg ctctggtcca ggatgtcgac      240
ggttccggct ctcctcagtt cccttcctct ctcgagtgga tcgccaacaa ccagctgtcc    300
gacggttctt ggggtgacca cctgctcttc tctgctcacg accgaatcat caacaccctg    360
gcctgtgtca ttgctctgac ctcttggaac gtccacccct ccaagtgcga aagggtctg       420 aacttcctcc gagagaacat ctgcaagctc gaggacgaga acgccgagca catgcccatt    480
ggcttcgagg tcaccttccc ctctctgatt gacattgcca gaagctcaa cattgaggtc       540 cccgaggaca cccccgctct caaggagatc tacgctcgac gagacatcaa gctcaccaag    600
atccccatgg aggttctcca aggtccccc accactctcc tccactctct cgagggtatg     660
cccgatctcg agtgggagaa gctgctcaag ctgcagtgca aggacggctc tttcctcttc    720
tcccctctct tccactgcct tcgccctcat cagaccaagg acgagaagtg tctccagtac    780
ctcaccaaca ttgtcaccaa gttcaacggt ggtgtcccca cgtctacccc cgttgacctc    840
tttgagcaca tctgggttgt tgaccgactc cagcgactcg gtatcgcccg atacttcaag    900
tccgagatca aggactgtgt cgagtacatc aacaagtact ggaccaagaa cggtatctgc    960
tgggcccgaa acacccacgt ccaggacatt gacgacaccg ccatgggctt ccgagttctg   1020
```

```
cgagcccacg gctacgatgt cacccccgat gtctttcgac agtttgagaa ggacggcaag   1080
tttgtctgtt tcgccggtca gtccacccag gccgtcaccg gtatgttcaa cgtctaccga   1140
gcttctcaga tgctcttccc cggtgagcga atcctcgagg acgccaagaa gttctcctac   1200
aactacctca aggagaagca gtccaccaac gagctgctcg acaagtggat cattgccaag   1260
gatctgcccg gtgaggttgg ctacgccctc gacatcccct ggtacgcctc tctgccccga   1320
ctggagactc gatactacct cgagcagtac ggtggtgagg acgatgtctg gatcggtaag   1380
accctgtacc gaatgggcta cgtttccaac aacacctacc tcgagatggc caagctcgac   1440
tacaacaact acgttgccgt cctccagctc gagtggtaca ccatccagca gtggtacgtc   1500
gacattggta tcgagaagtt cgagtccgac aacatcaagt ccgtccttgt ctcctactac   1560
ctcgctgctg cctccatctt cgagcccgag cgatccaagg agcgaattgc ctgggccaag   1620
accaccatcc tcgtcgacaa gatcacctcc atcttcgact cctcccagtc ctccaaggaa   1680
gatatcaccg ccttcattga caagttccga acaagtcct cctccaagaa gcactccatc   1740
aacggcgagc cctggcacga ggtcatggtt gctctcaaga aaactctcca cggctttgcc   1800
ctcgacgctc tgatgaccca ctctcaggac atccacccc agctccacca ggcctgggag   1860
atgtggctca ccaagctcca ggacggtgtt gatgtcactg ctgagctcat ggtccagatg   1920
atcaacatga ccgccggccg atgggtttcc aaggagctcc tcacccaccc ccagtaccag   1980
cgactctcca ctgtcaccaa ctctgtctgc acgacatca ccaagctcca caacttcaag   2040
gagaactcca ccaccgtcga ctccaaggtc caggagctgg tccagctcgt tttctccgac   2100 accccccgatg atctcgacca ggacatgaag cagaccttcc tgactgtcat gaaaactttc   2160
tactacaagg cctggtgcga ccccaacacc atcaacgacc acatctccaa ggtctttgag   2220
attgtgattt aa                                                       2232
```

<210> SEQ ID NO 24
<211> LENGTH: 2274
<212> TYPE: DNA
<213> ORGANISM: Artificial sequence
<220> FEATURE:
<223> OTHER INFORMATION: Kaurene synthase from Stevia rebaudiana CpO for
      expression in Yarrowia lipolitica

<400> SEQUENCE: 24

```
atgacctccc acggcggcca gaccaacccc accaacctca tcattgacac caccaaggag    60
cgaatccaga agcagttcaa gaacgtcgag atctccgttt cctcctacga caccgcctgg   120
gtcgccatgg tccctctcc caactcccc aagtctccct gcttccccga gtgtctcaac   180
tggctcatca caaccagct caacgacggc tcttggggtc tggtcaacca caccacaac   240 cacaaccacc cctcctcaa ggactctctc tcttccactc tcgcctgcat gttgctctc   300 aagcgatgga cgttggcga ggaccagatc aacaagggtc tgtctttcat tgagtccaac   360
ctcgcctccg ccaccgagaa gtcccagccc tcccccattg ctttgatat catcttcccc   420 ggtctgctcg agtacgccaa gaacctcgat atcaacctgc tctccaagca gaccgacttc   480
tctctcatgc tgcacaagcg agagctcgag cagaagcgat gccactccaa cgagatggac   540
ggctacctgg cctacatttc cgagggtctg gtaacctct acgactggaa catggtcaag   600
aagtaccaga tgaagaacgg ttccgttttc aactccccct ctgccaccgc tgctgccttc   660
atcaaccacc agaaccccgg ctgtctcaac tacctcaact ctctgctcga caagtttggt   720
aacgccgtcc ccactgtcta ccccccacgat ctcttcatcc gactctccat ggtcgacacc   780
```

| | |
|---|---|
| attgagcgac tcggtatttc ccaccacttc cgagtcgaga tcaagaacgt tctcgatgag | 840 |
| acttaccgat gctgggttga gcagagatgag cagatcttca tggacgttgt cacctgtgct | 900 |
| ctggccttcc gactcctccg aatcaacggt tacgaggttt cccccgaccc cctcgccgag | 960 |
| atcaccaacg agctggctct caaggacgag tacgccgccc tcgagactta ccacgcttct | 1020 |
| cacattctgt accaagagga tctgtcctcc ggcaagcaga ttctcaagtc cgccgacttc | 1080 |
| ctcaaggaga tcatctccac tgactccaac cgactctcca agctcatcca aggaagtc | 1140 |
| gagaacgctc tcaagttccc catcaacacc ggtctggagc gaatcaacac ccgacgaaac | 1200 |
| atccagctct acaacgtcga caacccga attctcaaga ccacctacca ctcttccaac | 1260 |
| atctccaaca ccgactacct gcgactcgcc gtcgaggact tctacacctg ccagtccatc | 1320 |
| taccgagagg agctcaaggg tctggagcga tgggttgtcg agaacaagct cgaccagctc | 1380 |
| aagtttgccc gacaaaagac tgcctactgc tacttctccg ttgctgccac cctctcttct | 1440 |
| cccgagctct ccgacgcccg aatctcttgg gccaagaacg gtatcctgac cactgttgtc | 1500 |
| gacgacttct ttgacattgg tggcaccatt gacgagctga ccaacctcat ccagtgcgtc | 1560 |
| gagaagtgga acgtcgacgt tgacaaggac tgttgttccg agcacgtccg aatcctcttc | 1620 |
| ctggctctca aggacgccat ctgctggatc ggtgacgagg ccttcaagtg gcaggctcga | 1680 |
| gatgtcactt cccacgtcat ccagacctgg ctcgagctca tgaactccat gctgcgagag | 1740 |
| gccatctgga cccgagatgc ctacgtcccc accctcaacg agtacatgga gaacgcctac | 1800 |
| gtcagctttg ctctcggtcc cattgtcaag cccgccatct actttgtcgg tcccaagctg | 1860 |
| tccgaggaga ttgtcgagtc ctccgagtac cacaacctct tcaagctcat gtccacccag | 1920 |
| ggccgactcc tcaacgatat ccactccttc aagcgagagt tcaaggaagg taagctcaac | 1980 |
| gccgttgctc tgcacctgtc caacggtgag tccggcaagg tcgaggaaga ggtcgtcgag | 2040 |
| gagatgatga tgatgatcaa gaacaagcga aaggagctca tgaagctcat cttcgaggag | 2100 |
| aacggctcca ttgtccccg agcctgcaag gacgccttct ggaacatgtg ccacgtcctc | 2160 |
| aacttcttct acgccaacga cgacggtttc accggcaaca ccattctcga caccgtcaag | 2220 |
| gacatcatct acaaccctct ggttctggtc aacgagaacg aggagcagag gtaa | 2274 |

<210> SEQ ID NO 25
<211> LENGTH: 1578
<212> TYPE: DNA
<213> ORGANISM: Artificial sequence
<220> FEATURE:
<223> OTHER INFORMATION: Kaurene oxidase from Giberella fujikuroi CpO
    for expression in Yarrowia lipolitica

<400> SEQUENCE: 25

| | |
|---|---|
| atgtccaagt ccaactccat gaactccacc tcccacgaga ctctcttcca gcagctcgtt | 60 |
| ctcggcctcg accgaatgcc cctcatggac gtccactggc tcatctacgt tgcctttggt | 120 |
| gcctggctct gctcctacgt catccacgtt ctgtcctctt cctccactgt caaggtcccc | 180 |
| gtcgtcggtt accgatccgt tttcgagccc acctggctcc tccgactgcg attcgtctgg | 240 |
| gagggtggtt ccatcattgg ccagggctac aacaagttca aggactccat cttccaggtc | 300 |
| cgaaagctcg gtaccgacat tgtcatcatc cctcccaact acattgacga ggtccgaaag | 360 |
| ctctcccagg acaagacccg atccgtcgag cccttcatca acgactttgc cggccagtac | 420 |
| acccgaggta tggtctttct gcagtccgat ctccagaacc gagtcatcca gcagcgactc | 480 |
| acccccaagc ttgtctctct caccaaggtc atgaaggaag agctcgacta cgctctgacc | 540 |

```
aaggagatgc ccgacatgaa gaacgacgag tgggttgagg tcgacatctc ttccatcatg    600
gtccgactca tctctcgaat ctccgcccga gttttcctcg gccccgagca ctgccgaaac    660
caggagtggc tcaccaccac cgccgagtac tccgagtctc tcttcatcac cggcttcatc    720
ctccgagttg tcccccacat tctccgaccc ttcattgctc tctgctgcc ctcttaccga    780 accctgctgc gaaacgtttc ttccggccga cgagtcattg gtgatatcat ccgatcccag    840
cagggtgacg gtaacgagga catcctctct tggatgcgag atgctgccac tggtgaggag    900
aagcagatcg acaacattgc ccagcgaatg ctcattctgt ctctcgcctc catccacacc    960
accgccatga ccatgaccca cgccatgtac gatctgtgtg cctgccccga gtacattgag   1020
cccctccgag atgaggtcaa gtccgtcgtt ggtgcttctg gctgggacaa gaccgctctc   1080
aaccgattcc acaagctcga ctctttcctc aaggagtccc agcgattcaa ccccgttttc   1140
ctgctcacct tcaaccgaat ctaccaccag tccatgaccc tctccgatgg taccaacatc   1200
ccctccggta cccgaattgc tgtccccctct cacgccatgc tccaggactc cgcccacgtc   1260
cccggtccca ctcctcccac tgagttcgac ggtttccgat actccaagat ccgatccgac   1320
tccaactacg cccagaagta cctcttctc atgaccgact cttccaacat ggcctttggc   1380
tacggtaagt acgcctgccc cggccgattc tacgcctcca cgagatgaa gctgactctg   1440 gccattctgc tcctccagtt tgagttcaag ctccccgacg gtaagggccg acccccgaaac   1500 atcaccatcg actccgacat gatccccgac ccccgagctc gactctgtgt ccgaaagcga   1560
tctctgcgtg acgagtaa                                                 1578
```

<210> SEQ ID NO 26
<211> LENGTH: 1578
<212> TYPE: DNA
<213> ORGANISM: Artificial sequence
<220> FEATURE:
<223> OTHER INFORMATION: kaurenoic acid 13-hydroxylase from Arabidopsis
      thaliana, codon-pair optimized for expression in Yarrowia
      lipolitica

<400> SEQUENCE: 26

```
atggagtctc tggttgtcca caccgtcaac gccatctggt gcattgtcat tgtcggtatc     60
ttctccgtcg gctaccacgt ctacggccga gctgttgtcg agcagtggcg aatgcgacga    120
tctctcaagc tccagggtgt caagggtcct cctcccctcca tcttcaacgg taacgttttcc    180 gagatgcagc gaatccagtc cgaggccaag cactgctccg gtgacaacat catctcccac    240
gactactctt cttctctgtt cccccacttt gaccactggc gaaagcagta cggccgaatc    300
tacacctact ccactggcct caagcagcac ctctacatca ccaccccga tggtcaag      360 gagctctccc agaccaacac cctcaacctc ggccgaatca cccacatcac caagcgactc    420
aaccccattc tcggtaacgg tatcatcacc tccaacggcc cccactggc ccaccagcga     480 cgaatcattg cctacgagtt cacccacgac aagatcaagg gtatggtcgg tctgatggtc    540
gagtccgcca tgcccatgct caacaagtgg gaggagatgt caagcgagg tggtgagatg    600 ggctgtgaca tccgagtcga cgaggacctc aaggatgtct ccgctgacgt cattgccaag    660 gcctgttcg gctcttcctt ctccaagggc aaggccatct ctccatgat ccgagatctg    720 ctcaccgcca tcaccaagcg atccgtcctc ttccgattca acggtttcac cgacatggtt    780
ttcggctcca gaagcacgg tgacgttgac attgacgctc tcgagatgga gctcgagtcc    840
tccatctggg agactgtcaa ggagcgagag attgagtgca aggacaccca caagaaggac    900
ctcatgcagc tcattctcga gggtgccatg cgatcttgtg acggtaacct gtgggacaag    960
```

```
tctgcttacc gacgattcgt tgtcgacaac tgcaagtcca tctactttgc cggccacgac    1020
tccaccgccg tttccgtttc ttggtgcctc atgctgctcg ctctcaaccc ctcttggcag    1080
gtcaagatcc gagatgagat tctgtcctcc tgcaagaacg gtatccccga cgccgagtcc    1140
atccccaacc tcaagaccgt caccatggtc atccaggaga ctatgcgact ctaccctccc    1200
gctcccattg tcggccgaga ggcctccaag gacattcgac tcggtgatct ggttgtcccc    1260
aagggtgtct gtatctggac cctcatcccc gctctgcacc gagatcccga gatctggggt    1320
cccgacgcca acgacttcaa gcccgagcga ttctccgagg tatctccaa ggcctgcaag    1380 taccccccagt cctacatccc ctttggcctc ggcccccgaa cctgtgtcgg caagaacttt    1440
ggtatgatgg aggtcaaggt cctcgtttct ctgattgtct ccaagttctc cttcactctg    1500
tctcccacct accagcactc tccctcccac aagctgctcg tcgagcccca gcacggtgtt    1560
gtcatccgag ttgtataa                                                  1578
```

<210> SEQ ID NO 27
<211> LENGTH: 2136
<212> TYPE: DNA
<213> ORGANISM: Artificial sequence
<220> FEATURE:
<223> OTHER INFORMATION: Cytochrome P450 reductase from Arabidopsis
      thaliana CpO for expression in Yarrowia lipolitica

<400> SEQUENCE: 27

```
atgtcctcct cttcttcttc ttccacctcc atgattgatc tcatggctgc catcatcaag     60
ggtgagcccg tcattgtctc cgaccccgcc aacgcctccg cctacgagtc cgttgctgcc    120
gagctgtcct ccatgctcat cgagaaccga cagtttgcca tgatcgtcac cacctccatt    180
gctgttctca ttggctgcat tgtcatgctc gtctggcgac gatctggctc cggtaactcc    240
aagcgagtcg agccccctcaa gcccctggtc atcaagcccc gagaagagga gatcgacgac    300
ggccgaaaga aggtcaccat cttctttggc acccagaccg gtactgctga gggcttcgcc    360
aaggctctcg gtgaggaagc caaggctcga tacgaaaaga cccgattcaa gattgtcgac    420
ctcgatgatt acgctgccga tgacgacgag tacgaggaga gctcaagaa agaggacgtt    480 gccttcttct tcctcgccac ctacggtgac ggtgagccca ccgacaacgc tgcccgattc    540
tacaagtggt tcaccgaggg taacgaccga ggcgagtggc tcaagaacct caagtacggt    600
gttttcggtc tgggcaaccg acagtacgag cacttcaaca aggttgccaa ggttgtcgac    660
gacatcctcg tcgagcaggg tgcccagcga ctcgtccagg tcggcctcgg tgatgatgac    720
cagtgcatcg aggacgactt cactgcctgg cgagaggctc tgtggcccga gctcgacacc    780
attctgcgag aggaaggtga caccgccgtt gccaccccct acaccgccgc cgtcctcgag    840
taccgagtct ccatccacga ctccgaggat gccaagttca cgacatcaa catggccaac    900 ggtaacggct acaccgtctt tgacgcccag caccctaca aggccaacgt cgccgtcaag    960
cgagagctcc acacccccga gtccgaccga tcttgtatcc acctcgagtt tgacattgct   1020
ggttccggtc tgacctacga gactggtgac cacgttggtg tcctctgtga aacctgtcc   1080 gagactgtcg acgaggctct gcgactcctc gacatgtccc ccgacactta cttctctctg    1140
cacgccgaga agaggacgg tactcccatc tcttcttctc tgcccctcc cttccctccc    1200 tgcaacctgc gaaccgctct gacccgatac gcctgcctcc tctcttctcc caagaagtct    1260
gctctcgttg ctctgccgc ccacgcctcc gaccccaccg aggctgagcg actcaagcac    1320
ctcgcctctc ccgctggcaa ggacgagtac tccaagtggg ttgtcgagtc ccagcgatct    1380
```

```
ctgctcgagg tcatggccga gttcccctcc gccaagcccc ctctcggtgt tttcttcgcc    1440
ggtgttgctc cccgactcca gccccgattc tactccatct cctcttcccc caagatcgcc    1500
gagactcgaa tccacgttac ctgtgctctg gtctacgaga agatgcccac cggccgaatc    1560
cacaagggtg tctgctccac ctggatgaag aacgccgttc cctacgagaa gtccgagaac    1620
tgttcctctg ctcccatctt tgtccgacag tccaacttca agctccgctc cgactccaag    1680
gtccccatca tcatgattgg ccccggtacc ggcctcgccc ccttccgagg cttcctgcag    1740
gagcgactcg ccctcgtcga gtccggtgtc gagctcggcc cctccgtcct cttctttggc    1800
tgccgaaacc gacgaatgga cttcatctac gaagaggagc tccagcgatt cgtcgagtcc    1860
ggtgctctcg ccgagctctc cgttgccttc tcccgagagg gtcccaccaa ggagtacgtc    1920
cagcacaaga tgatggacaa ggcctccgac atctggaaca tgatctccca gggcgcctac    1980
ctctacgtct gcggtgacgc caagggtatg gcccgagatg tccaccgatc tctgcacacc    2040
attgcccagg agcagggctc catggactcc accaaggccg agggtttcgt caagaacctc    2100
cagacctccg ccgatacct ccgagatgtc tggtaa                               2136
```

<210> SEQ ID NO 28
<211> LENGTH: 1446
<212> TYPE: DNA
<213> ORGANISM: Artificial sequence
<220> FEATURE:
<223> OTHER INFORMATION: UDP-glycosyltransferase from Stevia rebaudiana
      Cpo for expression in Yarrowia lipolitica

<400> SEQUENCE: 28

```
atggacgcca tggccaccac cgagaagaag ccccacgtca tcttcatccc cttccccgcc      60
cagtcccaca tcaaggccat gctcaagctc gcccagctcc tccaccacaa gggcctccag     120
atcacctttg tcaacaccga cttcatccac aaccagttcc tcgagtcctc cggcccccac     180
tgtctggacg tgctcccggg tttccgattt gagactatcc ccgatggtgt ctcccactcc     240
cccgaggcct ccatccccat ccgagagtct ctgctccgat ccattgagac taacttcctc     300
gaccgattca ttgatctcgt caccaagctc ccgatcctc ccacctgtat catctccgac     360
ggtttcctgt ccgttttcac cattgatgct gccaagaagc tcggtatccc cgtcatgatg     420
tactggactc tggctgcctg tggtttcatg ggtttctacc acatccactc tctgatcgag     480
aagggctttg ctcctctcaa ggacgcctcc tacctcacca acggttacct cgacaccgtc     540
attgactggg tccccggtat ggagggtatc cgactcaagg acttccccct cgactggtcc     600
accgacctca cgacaaggt tctcatgttc accaccgagg ctccccagcg atcccacaag     660
gtttcccacc acatcttcca caccttcgac gagctcgagc cctccatcat caagactctg     720
tctctgcgat acaaccacat ctacaccatt ggccccctcc agctcctcct cgaccagatc     780
cccgaggaga agaagcagac cggtatcacc tctctgcacg gctactctct cgtcaaggaa     840
gagcccgagt gcttccagtg ctccagtcc aaggagccca actccgttgt ctacgtcaac     900
tttggctcca ccaccgtcat gtctctcgag acatgaccg agtttggctg ggtctggcc     960 aactccaacc actacttcct gtggatcatc cgatccaacc tcgtcattgg cgagaacgcc    1020
gttctgcctc ccgagctcga ggagcacatc aagaagcgag gcttcattgc ctcttggtgc    1080
tcccaggaga aggttctcaa gcacccctc gtcggtggtt tcctgaccca tgcggctgg    1140 ggctccacca ttgagtctct gtccgctggt gtccccatga tctgctggcc ctactcctgg    1200
gaccagctca ccaactgccg atacatctgc aaggagtggg aggttggtct ggagatgggt    1260
```

| accaaggtca agcgagatga ggtcaagcga ctcgtccagg agctcatggg cgagggtggt | 1320 |
| cacaagatgc gaaacaaggc caaggactgg aaggagaagg cccgaattgc cattgccccc | 1380 |
| aacggctctt cttctctcaa cattgacaag atggtcaagg agatcactgt tctcgctcga | 1440 |
| aactaa | 1446 |

<210> SEQ ID NO 29
<211> LENGTH: 1422
<212> TYPE: DNA
<213> ORGANISM: Artificial sequence
<220> FEATURE:
<223> OTHER INFORMATION: variant of UDP-glycosyltransferase from Stevia
      rebaudiana Cpo for expression in Yarrowia lipolitica

<400> SEQUENCE: 29

| atggccacct ccgactccat tgttgacgac cgaaagaagc tccacattgt catgttcccc | 60 |
| tggctcgcct ttggccacat catccctat ctcgagcttt ccaagctcat tgcccagaag | 120 |
| ggccacaagg tttccttcct ctccaccacc aagaacattg accgactctc ctcccacatc | 180 |
| tctcccctca tcaactttgt caagctcacc ctcccccgag tccaggagct gcccgaggac | 240 |
| gccgaggcca ccactgatgt ccaccccgag gatatcccct acctcaagaa ggcctccgac | 300 |
| ggcctccagc ccgaggtcac tgagttcctc gagcagcact ctcccgactg gatcatctac | 360 |
| gactacaccc actactggct ccccgagatt gccaagtctc tcggtgtctc tcgagcccac | 420 |
| ttctccgtca ccaccccctg ggccattgct acatgggtc ccactgccga tgccatgatc | 480 |
| aacggttccg actaccgaac cgagcttgag gacttcaccg tccctcccaa gtggttcccc | 540 |
| ttccccacca ccgtctgctg gcgaaagcac gatctggccc gactcgtccc ctacaaggct | 600 |
| cccggtatct ccgacggtta cgaatgggc ctcgtcatca agggctgcga ctgtctgctc | 660 |
| tccaagacct accacgagtt cggtactcag tggctccgac ttctcgagga gctgcaccga | 720 |
| gtccccgtca tccccgttgg tctgctccct ccctccatcc ccggctctga caaggacgac | 780 |
| tcttgggttt ccatcaagga gtggctcgac ggccaggaga agggctccgt tgtctacgtt | 840 |
| gctctcggtt ccgaggttct cgtcacccag gaagaggttg tcgagcttgc tcacggtctg | 900 |
| gagctgtccg gtctgccctt cttctggcc taccgaaagc ccaagggtcc cgccaagtcc | 960 |
| gactccgtcg agcttcccga tggtttcgtc gagcgagtcc gagatcgagg tctggtctgg | 1020 |
| acctcttggg ctccccagct ccgaatcctc tcccacgagt ccgttgctgg tttcctcacc | 1080 |
| cactgcggtt ccggctccat tgtcgagggc ctcatgttcg ccaccctct catcatgctc | 1140 |
| cccatcttcg gtgaccagcc cctcaacgcc cgactccttg aggacaagca ggtcggtatc | 1200 |
| gagatccccc gaaacgagga agatggttct ttcacccgag actctgttgc cgagtctctg | 1260 |
| cgactcgtca tggtcgagga gagggtaag atctaccgag agaaggccaa ggagatgtcc | 1320 |
| aagctctttg gcgacaagga cctccaggac cagtacgtcg acgactttgt cgagtacctc | 1380 |
| cagaagcacc gacgagctgt tgccattgac cacgaaagct aa | 1422 |

<210> SEQ ID NO 30
<211> LENGTH: 1377
<212> TYPE: DNA
<213> ORGANISM: Artificial sequence
<220> FEATURE:
<223> OTHER INFORMATION: UDP-glycosyltransferase from Stevia rebaudiana
      Cpo for expression in Yarrowia lipolitica

<400> SEQUENCE: 30

| | |
|---|---:|
| atggagaaca agaccgagac taccgtccga cgacgacgac gaatcattct cttccccgtc | 60 |
| cccttccagg gccacatcaa ccccattctg cagctcgcca acgttctgta ctccaagggc | 120 |
| ttctccatca ccatcttcca caccaacttc aacaagccca agacctccaa ctaccccac | 180 |
| ttcactttcc gattcatcct cgacaacgac ccccaggacg agcgaatctc caacctgccc | 240 |
| acccacggtc tctggctgg tatgcgaatc cccatcatca cgagcacgg tgctgacgag | 300 |
| ctccgacgag agctcgagct gctcatgctc gcctccgaag aggacgagga agtctcctgt | 360 |
| ctgatcaccg atgctctgtg gtactttgcc cagtccgtcg ccgactctct caacctgcga | 420 |
| cgactcgttc tcatgacctc ctctctgttc aacttccacg cccacgtttc tctgccccag | 480 |
| tttgacgagc tcggttacct cgaccccgat gacaagaccc gactcgagga gcaggcttcc | 540 |
| ggtttcccca tgctcaaggt caaggacatc aagtccgcct actccaactg gcagattctc | 600 |
| aaggagattc tcggcaagat gatcaagcag accaaggcct cctccggtgt catctggaac | 660 |
| tccttcaagg agctcgagga gtccgagctc gagactgtca tccgagagat ccccgctccc | 720 |
| tctttcctca tcccccctgcc caagcacctc accgcttcct cctcttctct gctcgaccac | 780 |
| gaccgaaccg tctttcagtg gctcgaccag cagcccccctt cctccgtcct ctacgttttcc | 840 |
| ttcggctcca cctccgaggt cgacgagaag gacttcctcg agattgctcg aggcctcgtt | 900 |
| gactccaagc agtccttcct gtgggttgtc cgacccggct ttgtcaaggg ctccacctgg | 960 |
| gttgagcccc tgcccgatgg tttcctcggt gagcgaggcc gaattgtcaa gtgggtcccc | 1020 |
| cagcaggaag ttctggccca cggtgccatt ggtgccttct ggacccactc cggctggaac | 1080 |
| tccactctcg agtccgtctg cgagggtgtc cccatgatct ctccgactt tggcctcgac | 1140 |
| cagccccctca acgccgata catgtccgat gttctcaagg tcggtgtcta cctcgagaac | 1200 |
| ggctgggagc gaggtgagat tgccaacgcc atccgacgag tcatggtcga cgaggaaggt | 1260 |
| gagtacatcc gacagaacgc ccgagtcctc aagcagaagg ccgatgtctc tctcatgaag | 1320 |
| ggtggttctt cttacgagtc tctcgagtct ctcgtttcct acatctcttc tttgtaa | 1377 |

<210> SEQ ID NO 31
<211> LENGTH: 999
<212> TYPE: DNA
<213> ORGANISM: Artificial sequence
<220> FEATURE:
<223> OTHER INFORMATION: HSP promoter

<400> SEQUENCE: 31

| | |
|---|---:|
| gtgcaatcac atgttgctac tgtacctgct gtggaccacg cacggcggaa cgtaccgtac | 60 |
| aaatattttc ttgctcacat gactctctct cggccgcgca cgccggtggc aaattgctct | 120 |
| tgcattggct ctgtctctag acgtccaaac cgtccaaagt ggcagggtga cgtgatgcga | 180 |
| cgcacgaagg agatggcccg gtggcgagga accggacacg gcgagccggc gggaaaaaag | 240 |
| gcggaaaacg aaaagcgaag ggcacaatct gacggtgcgg ctgccaccaa cccaaggagg | 300 |
| ctattttggg tcgctttcca tttcacattc gccctcaatg ccactttgc ggtggtgaac | 360 |
| atggtttctg aaacaacccc ccagaattag agtatattga tgtgtttaag attgggttgc | 420 |
| tatttggcca ttgtggggga gggtagcgac gtggaggaca ttccagggcg aattgagcct | 480 |
| agaaagtggt agcattccaa ccgtctaagt cgtccgaatt gatcgctata actatcacct | 540 |
| ctctcacatg tctacttccc caaccaacat ccccaacctc ccccacacta agttcacgc | 600 |
| caataatgta ggcactcttt ctgggtgtgg gacagcagag caatacgag gggagattac | 660 |
| acaacgagcc acaattgggg agatggtagc catctcactc gacccgtcga cttttggcaa | 720 |

```
cgctcaatta cccaccaaat ttgggctgga gttgagggga ccgtgttcca gcgctgtagg    780
accagcaaca cacacggtat caacagcaac caacgccccc gctaatgcac ccagtactgc    840
gcaggtgtgg gccaggtgcg ttccagatgc gagttggcga accctaagcc gacagtgtac    900
tttttgggac gggcagtagc aatcgtgggc ggaaaccccg gtgtatataa aggggtggag    960
aggacggatt attagcacca acacacacac ttatactac                            999

<210> SEQ ID NO 32
<211> LENGTH: 300
<212> TYPE: DNA
<213> ORGANISM: Artificial sequence
<220> FEATURE:
<223> OTHER INFORMATION: pgm terminator

<400> SEQUENCE: 32
acttcgagct aatccagtag cttacgttac ccaggggcag gtcaactggc tagccacgag     60
tctgtcccag gtcgcaattt agtgtaataa acaatatata tattgagtct aaagggaatt    120
gtagctattg tgattgtgtg attttcgtct tgctggttct tattgtgtcc cattcgtttc    180
atcctgatga ggacccctgg aaccggtgtt ttcttagtct ctgcaatcgc tagtcttgtt    240
gctatgacag ttgcgtcgac actattcagg tcatctatcg gttattctga tattataata    300

<210> SEQ ID NO 33
<211> LENGTH: 403
<212> TYPE: DNA
<213> ORGANISM: Artificial sequence
<220> FEATURE:
<223> OTHER INFORMATION: pAgos_lox TEF1 promoter

<400> SEQUENCE: 33
taccgttcgt ataatgtatg ctatacgaag ttatgtcccc gccgggtcac ccggccagcg     60
acatggaggc ccagaatacc ctccttgaca gtcttgacgt gcgcagctca ggggcatgat    120
gtgactgtcg cccgtacatt tagcccatac atccccatgt ataatcattt gcatccatac    180
attttgatgg ccgcacggcg cgaagcaaaa attacggctc ctcgctgcag acctgcgagc    240
agggaaacgc tcccctcaca gacgcgttga attgtcccca cgccgcgccc ctgtagagaa    300
atataaaagg ttaggatttg ccactgaggt tcttctttca tatacttcct tttaaaatct    360
tgctaggata cagttctcac atcacatccg aacataaaca aca                      403

<210> SEQ ID NO 34
<211> LENGTH: 285
<212> TYPE: DNA
<213> ORGANISM: Artificial sequence
<220> FEATURE:
<223> OTHER INFORMATION: Agos tef1Ts_lox terminator

<400> SEQUENCE: 34
atcagtactg acaataaaaa gattcttgtt ttcaagaact tgtcatttgt atagttttt      60 tatattgtag ttgttctatt taatcaaat gttagcgtga tttatatttt ttttcgcctc    120
gacatcatct gcccagatgc gaagttaagt gcgcagaaag taatatcatg cgtcaatcgt    180
atgtgaatgc tggtcgctat actgctgtcg attcgatact aacgccgcca tccagtgtcg    240
aaaacgagct cataacttcg tataatgtat gctatacgaa cggta                    285
```